(12) United States Patent
Gempeler et al.

(10) Patent No.: US 6,994,984 B2
(45) Date of Patent: Feb. 7, 2006

(54) HEMATOLOGICAL ASSAY

(75) Inventors: Patrizia Maria Gempeler, Aesch (CH); Andreas Calatzis, München (DE)

(73) Assignee: Pentapharm AG, Basel (CH)

( * ) Notice: Subject to any disclaimer, the term of this patent is extended or adjusted under 35 U.S.C. 154(b) by 56 days.

(21) Appl. No.: 10/168,473

(22) PCT Filed: Dec. 14, 2000

(86) PCT No.: PCT/EP00/12753

§ 371 (c)(1),
(2), (4) Date: Aug. 29, 2002

(87) PCT Pub. No.: WO01/44819

PCT Pub. Date: Jun. 21, 2001

(65) Prior Publication Data

US 2003/0104508 A1 Jun. 5, 2003

(30) Foreign Application Priority Data

Dec. 15, 1999 (WO) ...................... PCT/EP99/09952

(51) Int. Cl.
*C12Q 1/37* (2006.01)
(52) U.S. Cl. ..................................................... 435/23
(58) Field of Classification Search .................. 435/23
See application file for complete search history.

(56) References Cited

U.S. PATENT DOCUMENTS

| | | | |
|---|---|---|---|
| 4,756,884 A | 7/1988 | Hillman et al. | |
| 4,861,712 A | 8/1989 | Bartl et al. | |
| 4,946,775 A | 8/1990 | Yin | |
| 5,059,525 A | 10/1991 | Bartle et al. | |
| 5,110,727 A | 5/1992 | Oberhardt | |
| 5,266,462 A * | 11/1993 | Hemker et al. | ............... 435/13 |
| 5,300,779 A | 4/1994 | Hillman et al. | |
| 6,284,475 B1 * | 9/2001 | Rand | ......................... 435/7.21 |

OTHER PUBLICATIONS

Nishibe, "The Assay of Factor V in Plasma Using a Synthetic Chromogenic Substrate", Clinica Chimica Acta 106 : 301-7 (1980).*
Nicolaes et al., "A Prothrombinase-based Assay for Detection of Resistance to Activated Protein C", Thrombosis and Haemostasis 76(3) : 404-10 (1996).*
Keller et al., "Thrombin-Catalyzed Activation of Recombinant Human Factor V", Biochemistry 34 (12) : 4118-24 (1995).*
Bokarewa et al., "Studies on Phospholipid Antibodies, APC-resistance and Associated Mutation in the Coagulation Factor V gene", Thrombosis Research 78 (3) : 193-200 (1995).*
Calatzis an et al.; "Prothrombinase-induced clotting time (PiCT); a New Assay for the Monitoring of Heparins and Hirudin": Abstract & Haemostasis; vol. 30, No. 1-2, 2000 p 50.
Huisse et al., "Prothromb in Clamart: Prothrombin Variant with Defective Arg 320-lie Cleavage by Factor Xa"; Thrombosis Research, vol 44, no 1; 1986; pp 11-21.
Kandrotas et al.; Heparin Pharmokinetics and Pharmacodynamics, Clin. Pharmacokinet., vol. 22, 1992 pp 359-374.
Oberhardt B.J. et al., "Dry reagent technology for rapid convenient measurements of blood coagulation and fibrinolysis", Clin. Chem. 1991, 37, pp 520-25.
van den Besselaar A.M.H.P., et al., "Multicenter evaluation of a new capillary blood prothombin time monitoring system Blood Coagulation and Fibrinolsysis", 1995, 6, pp 726-732.
Van Rijin J L M L et al; "Kinetic Studies of Prothrombin Activation Effect of Factor V-A and Pospholipids on the Formation of the Enzyme-Substrate Complex", Biochemistry, vol. 23 No. 20, 1984 pp 4557-4564.
Witt, "Test Systems with Syntehtic Peptide Substrates in Haemostaseology", Eur. J. Clin. Biochem., vol. 29, 1991 pp 355-374.

* cited by examiner

Primary Examiner—Sandra E. Saucer
(74) Attorney, Agent, or Firm—Jones Day

(57) ABSTRACT

A hematological assay is described in which the blood coagulation potential of a body fluid is assessed by reacting a sample of the body fluid with an amount of an activator reagent comprising: (a) a predetermined amount of factor Xa or a hematologically equivalent mutant thereof, and (b) a predetermined amount of factor Va, a hematologically equivalent mutant thereof or an enzyme activating endogenous factor V, (c) (optionally) phospholipids. The reagent may be dry (e.g. lyophilised) or in an aqueous solution preferably buffered to a pH from 6 to 10 (preferably 7 to 8), if desired incubating, if necessary inducing coagulation by the addition of one or more coagulation accelerants such as calcium chloride, and establishing a value indicative of the coagulation potential, e.g. by measuring the time to clotting on an optical coagulometer or through use of a chromogenic substrate. It is preferred to use at (b) factor V activator from purified Russell's Viper venom (RVV-V). An activator reagent is also described containing the components mentioned above preferably in one or more buffer solutions or in dried, e.g. lyophilised form.

29 Claims, 8 Drawing Sheets

Heptest® Dose Response

+ LMWH aXa U/ml   • UFH U/ml   ■ r-hirudin µg/ml

Heptest® Optical Signal (added LMWH)

a control, b 0.2 aXa U/ml, c 0.4 aXa U/ml, d 0.6 aXa U/ml,
e 0.8 aXa U/ml, f 1 aXa U/ml Principle of the new clotting assay Assay Dose Response + LMWH aXa U/ml   • UFH U/ml   ■ r-hirudin µg/ml Assay Optical Signal (aXa LMWH)

a control,  b 0.2 U/ml,  c 0.4 U/ml,  d 0.6 U/ml,  e 0.8 U/ml,  f 1 U/ml

Effect of additional factor Xa

LMWH: + 0 aXaU/ml  • 0.5 aXaU/ml  ■ 1 aXaU/ml

Effect of omitting incubation

+ LMWH aXa U/ml  • UFH U/ml  ■ hirudin µg/ml

Patient on oral anticoagulant treatment

◆ Heptest® reference plasma  ● Invention reference plasma
▲ Heptest® with anticoagulation  × Invention with anticoagulation Correlation after LMWH Treatment $R^2 = 0.9389$ Fig. 11a
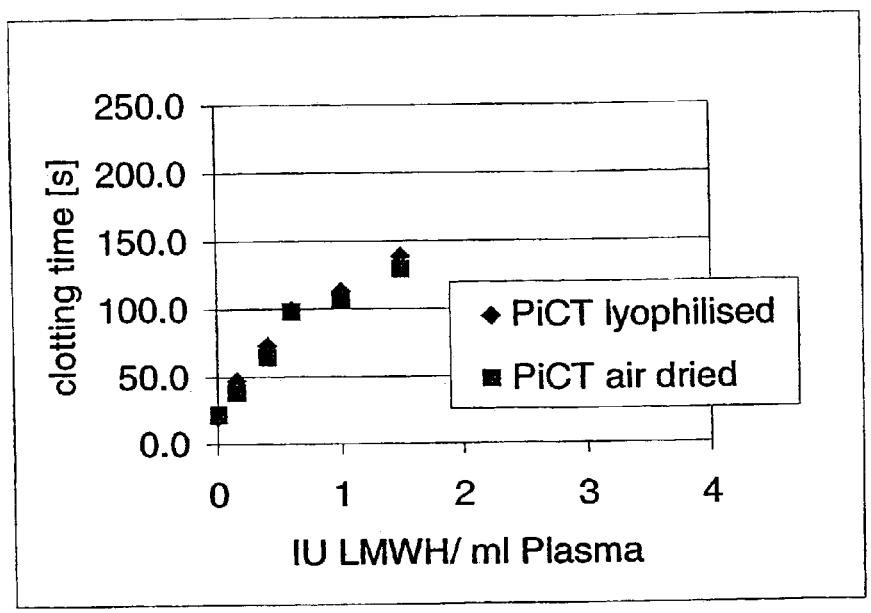
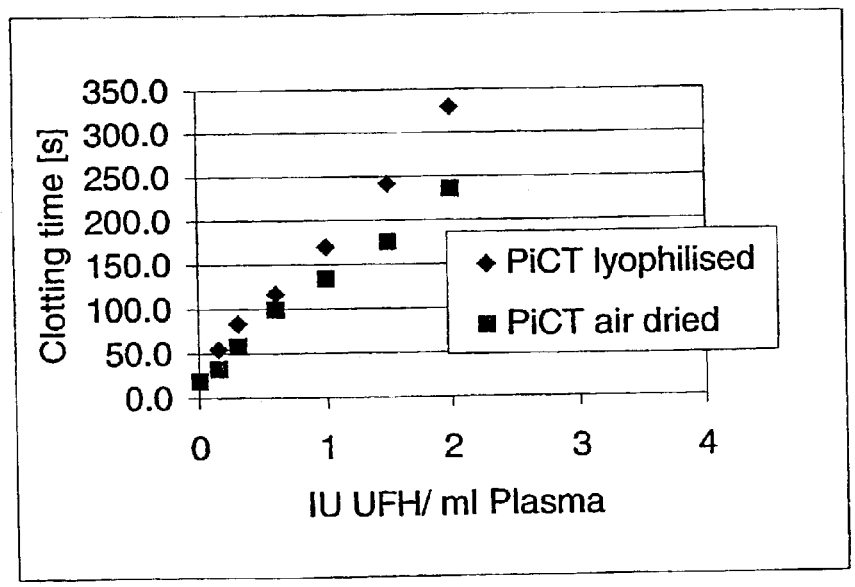
Fig. 11b Fig. 11c
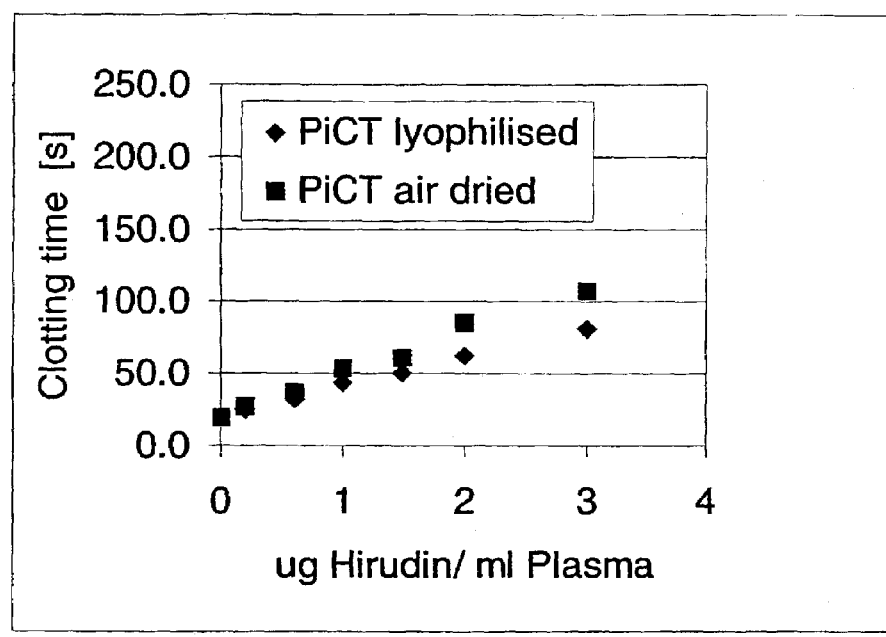
Fig. 12
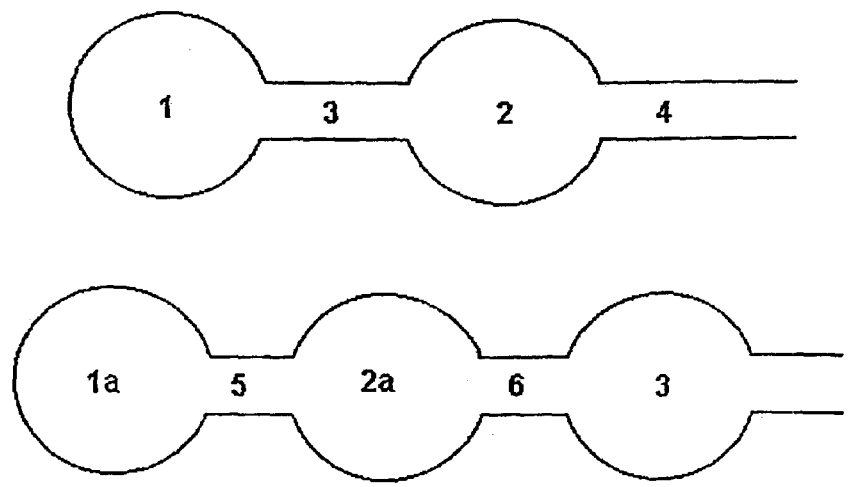
Fig. 13

HEMATOLOGICAL ASSAY

This is a national stage application of International Application PCT/EP00/12753, filed Dec. 14, 2000, which was published under PCT Article 21(2) as PCT Publication No. WO 01/448 19 in English, and which claims the benefit of International Application PCT/EP99/09952 filed Dec. 15, 1999. Both International Applications PCT/EPO00/12753 and PCT/EP99/09952 are hereby incorporated by reference in their entireties.

BACKGROUND

The present invention is concerned with the process of blood coagulation which involves an extremely complicated series of interactions generally known as the coagulation cascade, and which is well described in *Thrombosis and Hemorrhage,* Sec. Ed., 1998, published by Williams and Wilkins. It involves a series of sequential proteolytic actions directed towards coagulation and a complementary series of inhibitory actions involved with termination or inhibition of coagulation. For a better understanding of the invention FIG. 1 displays a part of the blood coagulation cascade. Activation of coagulation takes place along different pathways two of which: the Intrinsic pathway and the Extrinsic pathway are illustrated. These converge to form a common pathway leading to clot formation. Coagulation factors are inactive zymogens or inactive cofactors which, when cleaved by an active protease, are activated (as indicated by the subscript "a") and in turn activate the next zymogen or the precursor of a cofactor in the cascade.

In the extrinsic pathway, damaged tissue exposes Tissue factor which activates factor VII to its activated form VIIa. Tissue factor and factor VIIa form a complex which activates factor X at the common pathway.

In the intrinsic pathway, negatively charged surfaces are exposed to the action of factor XII and prekallikrein in the bloodstream. Factor XII is activated to factor XIIa which activates factor XI to factor XIa. Factor XIa activates factor IX to IXa. Factor IXa, Factor VIIIa, phospholipids and free calcium ions are required for the formation of the tenase complex, which activates factor X.

Factor Xa, factor Va, phospholipids and free calcium ions are required for the formation of the prothrombinase complex with which this invention is more particularly concerned, which activates prothrombin to thrombin.

Thrombin is the "key enzyme" of coagulation and is linked to many positive and negative feedback actions and also with the clotting process of blood itself. Positive feedbacks include: activation of factors V, VIII and XI. Negative feedbacks include: activation of protein C in the presence of thrombomodulin. The clotting process includes the cleavage of fibrinogen to fibrin and the activation of platelets.

A number of endogenous inhibitory interactions are important, and are presented in the Figure in italics and broken lines. Thus antithrombin, an inhibitor with a relatively broad spectrum whose activity is greatly enhanced by heparins, heparinoids and glycosaminoglycans, inhibits factor Xa, thrombin, factor XIa and factor XIIa. Heparin cofactor II is a more specific endogenous inhibitor which binds to thrombin and whose activity is also accelerated by heparin and additionally by dermatan sulfate. Activated Protein C inactivates factor VIIIa and factor Va. Tissue factor pathway inhibitor (TFPI) inhibits factor Xa and the tissue factor/factor VIIa complex in a factor Xa dependent fashion.

An appropriate equilibrium of activating and inhibiting factors is necessary for the physiological function of the coagulation system. In certain situations, e.g. hemophilia or lupus, essential factors are missing or materials (anticoagulants) are present which interfere with the coagulation system.

Also substances from animal origin can interfere with coagulation factors. For example hirudin, a protein from the salivary gland of the medicinal leech is a very potent thrombin inhibitor. Proteins from snake venoms can simulate certain factors and lead to coagulation and clotting. In particular some snake venoms activate factor X and/or factor V and can be used in in vitro assays for anticoagulants.

The dependence of the formation of the prothrombinase and tenase complexes on the presence of free calcium ions allows the temporary anticoagulation, e.g. with citrate (or other ionic complexing agent), of a blood sample. This allows the transport and centrifugation of a sample without clotting and also allows the performance of certain analytic reactions without the formation of said complexes.

Subsequent addition of calcium ions can immediately stimulate the activation of prothrombin to thrombin in the presence of phospholipids.

It is often necessary to treat blood with substances having a coagulating (in case of bleeding complications) or anticoagulating effect (for the prevention or treatment of thrombotic complications and during interventions which bring blood into contact with artificial materials, e.g. during extracorporeal blood circulation).

A successful long-term anticoagulation is possible with vitamin K antagonists such as warfarin or other coumarin-derived oral anticoagulants. These substances lead to impaired coagulation activity of the blood by interfering with the formation of certain coagulation factors. As they do not inhibit already formed coagulation factors they need several days, however, until a stable anticoagulation is achieved. In many situations rapid anticoagulation is necessary. One strategy for attaining anticoagulation in patients is the direct or indirect inhibition of activated coagulation factors. The inhibition of certain factors can be achieved using heparins and heparinoids, which require antithrombin and/or heparin cofactor II from plasma, and direct natural or synthetic inhibitors of factor IIa (thrombin) and Xa (e.g. hirudin, argatroban, tick anticoagulant). All these substances mainly target activated factor X (FXa) and/or thrombin. It is important to use an appropriate intensity of anticoagulation since both too high as well as inappropriately low anticoagulation might cause a loss of organ tissue or even death of the patient.

Some anticoagulant drugs e.g. unfractionated heparin (UFH) possess highly variable pharmacokinetics and their use necessitates monitoring of the patient's condition by assaying plasma from the treated patient and, where necessary, adaptation of the individual anticoagulant dosage.

Other anticoagulant strategies such as use of the low molecular weight heparins (LMWH) do not routinely require monitoring of the anticoagulant effect, as the pharmacokinetics are usually less variable. LMWH, containing only part of the glycosaminoglycan heparin chain, is less active than UFH and often considered safer to use. Also with LMWH there are cases where the laboratory assessment of the drug effect is mandatory, e.g. bleeding complications under anticoagulant treatment, suspected or manifestly impaired clearance of the drug (e.g. due to renal dysfunction), unusual pharmocokinetics (e.g. in children or strongly obese patients) or suspected or potential under- and over-dosage. Prolongation of coagulation is dependent on the concentration of anticoagulant in the sample.

The European Pharmacopeial Commission has adopted a standard potency evaluation for LMWH in terms of anti-factor Xa activity (aXa).

Known Coagulation Assays

Methods for measuring the effect on coagulation and/or the concentration in blood or plasma of direct or indirect inhibitors of activated coagulation factors include:

(a) the assessment of inhibition of coagulation factors (e.g. FIIa and FXa) using chromogenic substrate analysis and (b) so-called "clotting methods", e.g. the aPTT assay (activated partial thromboplastin time), the ACT assay (activated clotting time), the TT assay (thrombin time), the ECT assay (ecarin clotting time) and the Heptest® assay. The clotting methods are characterised by the fact that coagulation is activated by different regimens and the time from coagulation activation until detection of clotting in the sample is measured. The clotting time can be converted into direct concentration units by establishing a calibration curve with appropriate calibrating reagents.

Analysis of Anti-Factor Xa and Anti-Factor IIa Using Chromogenic Substrates

Usually a plasma sample is added to a reagent containing a defined amount of factor IIa or factor Xa (in certain assays antithrombin is also added). During an incubation period factor Xa/IIa is partly inactivated by the anticoagulant itself or by complexes of the anticoagulant with endogenous or exogenous antithrombin. A chromogenic substrate is added and degraded by residual factor Xa/IIa, enhancing optical density which is detected optically. Using a calibration curve the anti-factor Xa/IIa activity or the anticoagulant concentration is calculated.

These methods allow a specific assessment of anticoagulant concentration. However, they are relatively expensive and require specialised instrumentation and are therefore not widely applied in clinical practice. Moreover, the interaction of the anticoagulant with the patient's coagulation system is not assessed and the in vivo situation is not directly reflected.

The aPTT Assay

A blood or (more usually) a plasma sample is added to a reagent containing a contact activator (often substances with negatively charged surfaces like ellagic acid, celite or kaolin) and phospholipids, and is incubated for 2–10 minutes in the absence of calcium ions. The time recorded from the addition of $Ca^{2+}$ to the sample until detection of fibrin formation is the activated partial thromboplastin time (aPTT).

The aPTT assay has the advantages that it is a widely available test, the clotting method is simple and a large experience base for the monitoring of anticoagulant therapy exists. Although the aPTT is a relatively poorly standardised method, it is frequently employed for the monitoring of unfractionated heparin (UFH), whereas LMWH cannot be monitored with this assay due to its poor responsiveness. In addition to its low sensitivity to LMWH, the assay suffers from a non-linear dose-response relationship to direct thrombin inhibitors like hirudin, too high a sensitivity to UFH, poor standardisation among different instruments, reagents, even different lots of the same reagent. Also the dose response curve for heparin is not linear.

Regarding the mechanism of the aPTT assay, it must be stated that the initiation of coagulation by contact activation (the so-called contact phase) is not part of the physiological hemostatic pathway in the body. The contact phase is difficult to standardise, which is one of the reasons for the very poor standardisation of the assay. Many factors take part in the coagulation activation in the aPTT assay (XII, XI, VIII, IX, X, V, II) while inhibition of factors X and II is believed to be the main pathway of anticoagulant therapy using heparins, heparinoids and the direct inhibitors. For these reasons, the aPTT assay neither gives a very realistic estimation of the anticoagulation achieved in the patient, nor assesses anticoagulation with an appropriate specificity to the anticoagulant treatment. In addition, the assay is also sensitive to the presence of lupus anticoagulants.

The ECT Assay

The Ecarin clotting time assay is a clot based assay used for monitoring the effect of direct antithrombin agents. Ecarin, a purified protease obtained from the venom of the snake *Echis carinatus*, converts prothrombin to meizothrombin (a precursor of thrombin), producing a clotting end point in citrated whole blood and plasma. Antithrombin agents such as hirudin bind to meizothrombin prolonging the Ecarin clotting time. The ECT assay is highly affected by low prothrombin levels of the sample plasma.

The ACT Assay

This method consists in principle in the addition of blood to kaolin or celite, and measurement of the time interval until fibrin formation in the sample. This method is widely available. It is a point-of-care method with a short turn-around time and a broad measuring range which allows monitoring of high-dose heparinisation during cardiovascular surgery.

The ACT assay has many limitations: it has a poor correlation to the anticoagulant concentration (as assessed by chromogenic substrate analysis), low sensitivity to lower heparin concentrations (up to 0.7 U UFH/ml with a normal ACT), low sensitivity to LMWH, long clotting times and a very strong dependence on the patient's coagulation factors. There is poor standardisation of different clinically applied ACT methods.

The Thrombin Time Assay

The method consists in the addition of a certain amount of thrombin to the plasma sample and assessment of the time interval until clotting is detected. The method has the advantage of specifically assessing thrombin inhibition. Although this simple test is a direct measure for the antithrombin activity in plasma, it is not widely used due to its poor reliability and bad standardisation. In addition, no assessment of factor Xa inhibition is possible. The narrow measuring range is strongly dependent on the added thrombin concentration and different results can be obtained in response to thrombin concentration, species, presence of calcium and the volume ratio of thrombin and sample.

The Heparin Assay According to Yin (Presented in 1973)

The assay is based in principle on the incubation of a citrated plasma sample with bovine factor Xa. After a certain incubation time, a reagent containing phospholipids and bovine plasma is added followed by a calcium chloride solution for re-calcification.

This test allows a sensitive assessment of LMWH and UFH by a clotting method. However, it involves a relatively complicated three-step procedure and requires bovine plasma (which might limit the realistic estimation of the anticoagulant effect).

Heptest® Assay (Variation of the Yin Assay (Presented in 1987)

This assay, described in U.S. Pat. No. 4,946,775, consists in principle in the incubation of a sample of plasma or blood with factor Xa. After a certain incubation period, a reagent containing calcium chloride, phospholipids and a bovine plasma fraction is added and the time until detection of clotting is recorded. The bovine plasma fraction is reported by the manufacturer to be rich in factor V and fibrinogen, while it is depleted of prothrombin and other coagulation factors and thus will not clot by itself.

Like the original assay of Yin, the method provides a sensitive assessment of LMWH and UFH in a relatively simple clotting assay. However the Heptest® has a low sensitivity to direct thrombin inhibitors such as hirudin; high standardisation of the bovine plasma fraction is mandatory; the effect of the bovine plasma fraction on the patient's coagulation system is not absolutely defined and its performance on optical analysers can be a problem as the optical signal is not conclusive, as will become apparent. Although the Heptest® is a simple method it is not very widely used.

The chemistry and pharmacology of heparin and assays such as those above outlined are described in Thrombosis and Hemorrhage (op. cit.), and Kandrotas, R. J., *Heparin Pharmokinetics and Pharmacodynamics*, Clin. Pharmacokinet., vol. 22, 1992, pages 359–374.

Although most known assays are carried out using liquid reagents, systems have been developed, generally for point-of-care application, in which the reagents are supported in a dry state. Examples of such systems are described in U.S. Pat. Nos. 4,756,884, 4,861,712, 5,059,525, 5,110,727 and 5,300,779 and EP-A-680727.

The present invention is aimed at providing a simple and reliable hematological assay which is both sensitive and adjustable in sensitivity to cover the monitoring of a variety of anticoagulants, notably LMWH, UFH, heparinoids, dermatan sulphate, natural or synthetic inhibitors of factor Xa and inhibitors of factor IIa such as argatroban or hirudin, and in its preferred form provides a stable base line when used with optical coagulometers. The invention has many applications in addition to the monitoring of anticoagulant treatment as will become apparent.

The following definitions are used hereafter:

Blood Coagulation Potential

Generally speaking the blood coagulation potential represents the ability of a patient's blood to coagulate or more specifically its ability to activate or inhibit coagulation factors. This is defined for convenience in this specification as a value, which may be given in terms of comparison with, or ratio to, a normal value or standard, of the ability of a sample, e.g. of human whole blood or plasma, or of other mammalian body fluid containing whole blood or plasma, to coagulate to the point of thrombin formation or clotting. The value may be measured in terms of the time taken from induction of coagulation e.g. by the addition to a sample of one or more coagulation accelerants such as phospholipids and calcium ions. However a value indicative of the coagulation potential can be (or can be inferred from) an indirectly measured value, e.g. an indicator value from an added analytical accessory agent, e.g. a chromogenic substrate. This may give a value e.g. for the activity of a component such as factor Xa (which activates prothrombin to thrombin) or of the activity of thrombin.

Coagulation Accelerant

This is defined as a material or substance or mixture of such which greatly speeds up the rate of thrombin formation.

It is preferably a substance which completes the group of substances necessary to establish the prothrombinase complex. Thus the fully assembled prothrombinase complex catalyses thrombin formation at a rate that is 300,000 times more efficient than factor Xa acting alone. In addition to factors Va and Xa the prothrombinase complex requires the presence of phospholipid (or platelets) and calcium ions (although other ions can be substituted.)

Analytical Accessory Agent

This is defined as an agent added to a reaction system, e.g. to a sample prior to or, more normally, following treatment to enable the provision of a conveniently observable or otherwise detectable activity. An accessory agent commonly used is a chromogenic substrate: a peptide with distinctive coloured groups which are released when the substrate is acted on by e.g. factor Xa and/or thrombin. Such agents can be specifically designed either for the detection of factor Xa activity or for the detection of thrombin formation. The use of peptide substrates is discussed in Witt, Irene, *Test Systems with Synthetic Peptide Substrates in Haemostaseology*, Eur. J. Clin. Chem. Clin. Biochem., vol. 29, 1991, pages 355–374.

SUMMARY OF THE INVENTION

According to a first aspect, the invention provides an activator reagent for use in blood coagulation assays comprising in combination (a) a predetermined amount of factor Xa or a hematologically equivalent mutant thereof, and (b) a predetermined amount of factor Va, a hematologically equivalent mutant thereof or an enzyme activating endogenous factor V, The components may be present in combination in an aqueous solution, preferably buffered. The pH may vary over a wide range, e.g. 6 to 10, preferably 6 to 9 and more preferably 7 to 8, optimum 7.4.

Particularly in certain point-of-care systems the components (a) and (b) may be in a dry state (preferably lyophilised) e.g. in or on a supporting matrix such as a fleece or chamber surface, or in separate matrices. The components will normally re-enter solution upon the application of a sample of blood or plasma or other body fluid to be analysed.

The activator reagent may also contain a predetermined amount of phospholipid, especially when the sample is of plasma.

The ingredients (a) and (b) used in the activator reagent are preferably in a purified form substantially free from other blood components such as factors and cofactors whether in activated form or not, since such impurities might affect the results obtained and/or the stability of the test system employed.

Preferably (b) consists essentially of snake venom containing factor V activator and depleted in factor X activating components. Most preferably (b) consists essentially of factor V activator from purified Russell's Viper venom (RVV-V).

The activator reagent may consist essentially of:

a predetermined amount from 0.01 to 10 nkat/ml factor Xa, a predetermined amount from 0.05 to 10 (preferably 5) U/ml RVV-V, and (optionally) a predetermined amount from 1 to 200 µg/ml phospholipids, in an aqueous buffer solution containing from 10 to 100 mM Tris/HCl, from 0.6 to 1.2% w/v NaCl and from 0.1 to 1.0% w/v albumin.

A preferred activator reagent consists essentially of
0.4 nkat/ml factor Xa,
4 U/ml RVV-V, and
50 µg/ml phospholipids from rabbit brain cephalin, in an aqueous buffer solution containing 50 mM Tris/HCl, 0.9% w/v NaCl and 0.5% w/v albumin at a pH of 7.4.

Another preferred activator reagent consists essentially of
0.2 nkat/ml factor Xa,
2 U/ml RVV-V,
25 µg/ml phospholipids from rabbit brain cephalin, and in an aqueous buffer solution containing 25 mM Tris/HCl, 0.45% w/v NaCl and 0.25% w/v albumin, and 12.5 mM $CaCl_2$ at pH 7.4.

The invention also includes a lyophilised preparation of an activator solution as described above.

According to a second aspect of the invention there is provided a hematological assay in which the blood coagulation potential of a body fluid is assessed by reacting a sample of the body fluid with a amount of an activator reagent as described above, if necessary inducing coagulation by the addition of one or more coagulation accelerants, and establishing a value indicative of the coagulation potential.

Although it is normal to employ an aqueous buffer solution as a medium for the activator reagent, the use of a buffer is not always necessary.

While the preferred assays to be described are carried out on samples of predetermined amount, e.g. weight or volume of blood or plasma, the invention is applicable in point-of-care systems which do not necessarily require an exact amount. An example of such a point-of-care system is the CoaguChek® system available from Roche Diagnostics, Mannheim.

The required value may be established by measurement of the time for a said sample of predetermined amount to a reach a (directly or indirectly) detected onset of clotting, e.g. using an optical or mechanical coagulometer, or alternatively by the addition to the treated sample of an analytical accessory agent providing a detectable value. The analytical reagent may be a synthetic substrate specific to measurement of thrombin activity or of factor Xa activity and detecting the appropriate activity. Although chromogenic substrates are better known and generally preferred, a substrate having fluorogenic, amperogenic or luminogenic properties may be utilised.

The required value may also be established by addition to the reaction system of particles exhibiting mechanical, magnetic or electrical behaviour during coagulation and detecting appropriate behaviour.

Usually the value obtained with a said sample of predetermined amount is compared with that of one or more standards or reference samples to assess the coagulation potential. The reference sample may be a comparable sample of normal body fluid, e.g. blood or plasma or comprising blood or plasma.

The assay may be used for the determination of a blood coagulation component or treatment additive in a sample of body fluid comprising a predetermined amount of human or animal blood or plasma by comparing the coagulation potential with that of one or more standards. The coagulation potential may be compared with that of a comparable sample of normal body fluid and/or with that of a comparable sample of body fluid lacking the said component (or additive) or containing a known excess of the said component (or additive).

In a preferred assay the said value is established by detecting one of:
(i) the time from such addition to the onset of clotting,
(ii) the time from such addition to the detection of free thrombin activity,
(iii) the thrombin activity, or
(iv) the factor Xa activity.

Preferably the activator reagent includes a predetermined amount of natural or synthetic phospholipids or platelets and the method includes the addition to the reaction system of a coagulation accelerant comprising a predetermined amount of calcium (or functionally equivalent) ions.

It is preferred to utilise calcium ions as the coagulation accelerant. Phospholipids, preferably in predetermined amount, are normally added in an initial stage, e.g. in the activator reagent and/or prior to an incubation step although the invention includes the possible utilisation of phospholipids as an accelerant; in such a case calcium ions could be added with the activator reagent The assay is preferably conducted on human plasma, but is applicable to human whole blood (or animal blood or plasma). In the preferred assay utilising calcium-bound plasma or whole blood, preferably of human origin, no prothrombinase complex is formed until coagulation is initiated by the addition of calcium ions or other coagulation accelerant. It is believed that prior to establishment or assembly of the prothrombinase complex, factor Xa, added in the inventive assay, is progressively inactivated by any anticoagulant present which is effective against factor Xa. When the prothrombinase complex has been established factor Xa is protected against any further inactivation and the final activity can be determined in a stable manner.

The assay of the invention is particularly useful for monitoring the effect upon the blood coagulation of a patient of a dosage of anticoagulant especially natural or synthetic inhibitors of factor Xa and/or thrombin (factor IIa), and in particular unfractionated heparin (UFH), low molecular weight heparins (LMWH), dermatan sulphate, argatroban, modified hirudin and hirudin. It may be used for monitoring the effect upon the blood coagulation of a patient of a dosage of antibody against one or more blood coagulation components or for assessing the blood coagulation potential of a patient suspected of a deficiency or superabundance of one or more blood coagulation components such as coagulation factors, which may be anticoagulant or coagulant enzymes or proenzymes.

It may be used for assessing the blood coagulation potential of whole blood or plasma suspected of the presence of an antibody against one or more blood coagulation components, e.g. lupus anticoagulant.

It is preferred to employ, as a source of the said enzyme activating endogenous factor V, a snake venom containing a factor V activating component and depleted in factor X activating component. The preferred source is factor V activator from purified Russell's Viper venom (RVV-V). This is described in e.g. Tokunaga et. al., *The Factor V-activating Enzyme (RVV-V) from Russell's Viper Venom*, Journal of Biological Chemistry, vol. 263 1988, pages 17471–17481 and is obtainable commercially from Pentapharm AG, Basel. Other possible venoms (suitably purified to deplete factor X activating component) include those of *Vipera lebetina, Bothrops* species, *Akgistrodon* species and *Echis* species.

A preferred method comprises the steps of:
mixing a sample of the body fluid with an amount of the activator reagent,
incubating the mixture,
adding a said accelerator, (and optionally an analytical accessory agent), and
establishing a value indicative of the coagulation potential.

In particular, the preferred assay comprises the steps of i. preparing an activator reagent containing:
   a predetermined amount from 0.01 to 10 nkat/ml factor Xa,
   a predetermined amount from 0.05 to 10 (preferably 5) U/ml RVV-V, and
   (optionally) a predetermined amount from 1 to 200 μg/ml phospholipids, in an aqueous buffer solution containing from 10 to 200 mM Tris/HCl, from 0.6 to 1.2% w/v NaCl and from 0.01 to 1.0% w/v albumin, ii. mixing a predetermined amount from 1 to 100 μl citrated (or otherwise Ca-bound), platelet-poor plasma with a predetermined amount from 1 to 100 μl of the activator reagent, iii. incubating the mixture, iv. adding a predetermined amount from 10 to 100 μl of from 2 to 200 (preferably 100) mM $CaCl_2$, v. optionally adding an analytical accessory agent providing a detectable value, and vi. establishing the said value.

The buffer is preferably at a pH from 6 to 10, preferably 6 to 9, more preferably 7 to 8 and most preferably pH 7.4

More preferably the method comprises the steps of i. preparing an activator reagent containing:
   0.4 nkat/ml factor Xa,
   4 U/ml RVV-V, and
   50 μg/ml phospholipids from rabbit brain cephalin, in an aqueous buffer solution containing 50 mM Tris/HCl, 0.9% w/v NaCl and 0.5% w/v albumin at pH 7.4, ii. mixing 50 μl citrated platelet-poor plasma with 50 μl of the activator reagent, iii. incubating the mixture for 3 minutes at 37° C., iv. adding 50 μl of from 25 mM $CaCl_2$, and v. optionally adding an analytical accessory agent providing a detectable value, and vi. establishing the said value.

While the incubation step is normally used, in a modification of the assay described above useful for assessing high concentrations of heparin and similar anticoagulants the assay may be carried out in the absence of incubation. A preferred assay of this kind comprises the steps of i. preparing an activator reagent containing:
   0.2 nkat/ml factor Xa,
   2 U/ml RVV-V,
   25 μg/ml phospholipids from rabbit brain cephalin, in an aqueous buffer solution containing 25 mM Tris/HCl, 0.45% w/v NaCl and 0.25% w/v albumin, and 12.5 mM $CaCl_2$, at pH 7.4 ii. mixing 50 μl citrated, platelet-poor plasma with 100 μl of the activator reagent, iii. optionally adding an analytical accessory agent providing a detectable value, and iv. establishing the said value.

Preferably the said value is established by measuring the time from addition of $CaCl_2$ to the onset of clotting using an optical coagulometer.

In an assay employed for assessing the presence and/or concentration of a suspected coagulant or anticoagulant component in a plasma sample the sample may be diluted in plasma depleted only in the suspected coagulant or anticoagulant and the value established compared with that found with the depleted plasma and/or normal plasma.

A plasma sample may also be pre-diluted with normal plasma, a plasma fraction or one or more single coagulation factors so as to reduce the influence of matrix effects or to minimize the dependency of plasma coagulation factors, or it may be treated with a substance inactivating heparin or heparin-like substances thereby enhancing specificity to non-heparin anticoagulants. The assay may be carried out on a plasma sample which has been treated with a substance which activates or inactivates one or more coagulation factors.

The invention includes a kit for use in blood coagulation assays comprising in combination:

(i) an activator reagent as described above or separate components thereof, (ii) control and/or calibration samples, and (iii) one or more optional accessories selected from an aqueous solution of a calcium (or equivalent) salt of stated concentration, an analytical accessory agent, normal plasma, one or more plasma fractions, one or more coagulation factors, water and/or one or more buffer solutions. The kit will include instructions for carrying out an assay as described. Equivalent dried, e.g. lyophilised preparations can be used.

The analytical accessory agent may comprise one or more solutions or dried, e.g. lyophilised preparations of synthetic substrates for thrombin and/or factor Xa determination.

BRIEF DESCRIPTION OF THE DRAWINGS

Preferred forms of the invention are hereafter described with reference to the accompanying drawings, in which:

FIGS. 11a, 11b, 11c are graphs similar to FIG. 5 showing performance with dry reagents, FIG. 12 is a diagrammatic illustration of a capillary testing device, and FIG. 13 is a diagrammatic illustration of a different form of capillary testing device.

PREFERRED FORMS OF THE INVENTION

Figure 2:
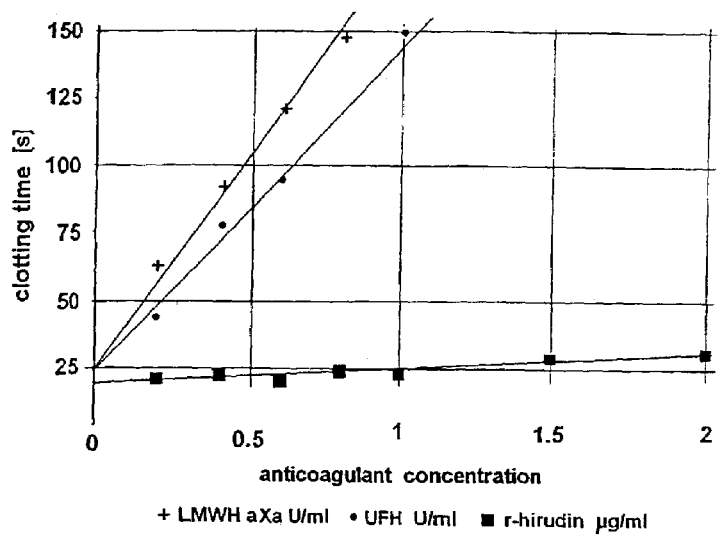
FIG. 2 is a graph illustrating typical dose response lines for LMWH, UFH and hirudin in a Heptest® assay.

For comparison with the assay according to the invention, FIG. 2 shows the dose-response relationship of the Heptest® with the common anticoagulants LMWH, UFH and recombinant hirudin (r-hirudin) in human normal reference plasma. This figure demonstrates the relatively poor responsiveness of the Heptest® for these direct thrombin inhibitors, in this case of hirudin.

Figure 3:
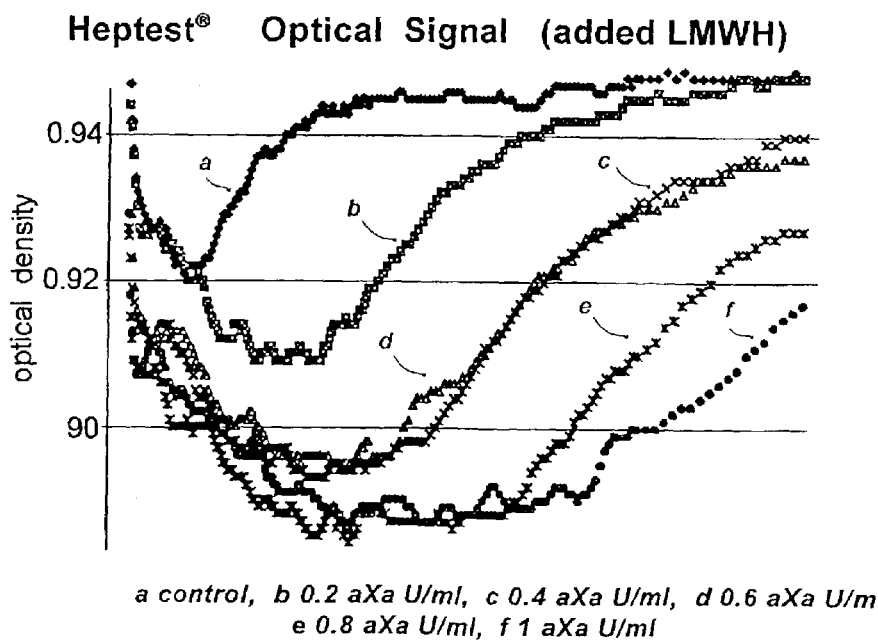
FIG. 3 is a graph showing optical signal curves produced in a typical Heptest® assay.

FIG. 3 shows optical signals of the Heptest® assay on the Behring Coagulation System (BCS) microcoagulometer at 405 nm. The baseline of the combination sample (citrated plasma prepared as recommended in the Heptest® package) is not stable. A decrease of absorbency does not allow the exact detection of the beginning of clot formation. The entire reaction curve displays noise which may have a negative influence on precision, a disadvantage when modern automated coagulometers are used for endpoint detection.

A preferred assay according to the invention permits the assessment of the coagulation potential of samples using a clotting method, based on the use of two, and preferably three, activating agents in predetermined concentrations together with the use of calcium ions, normally to initiate the beginning of clotting. Although this method, like the Yin assay and the Heptest® assay relies upon the formation of a prothrombinase complex on phospholipids, many or most of the disadvantages mentioned, including poor optical signals as described with reference to FIG. 3, are overcome. This new method is sensitive for UFH, LMWH and hirudin and other direct or indirect factor Xa and/or thrombin inhibitors in the relevant concentration ranges and in clinical practice. Moreover, it provides very stable optical signals.

Figure 1:
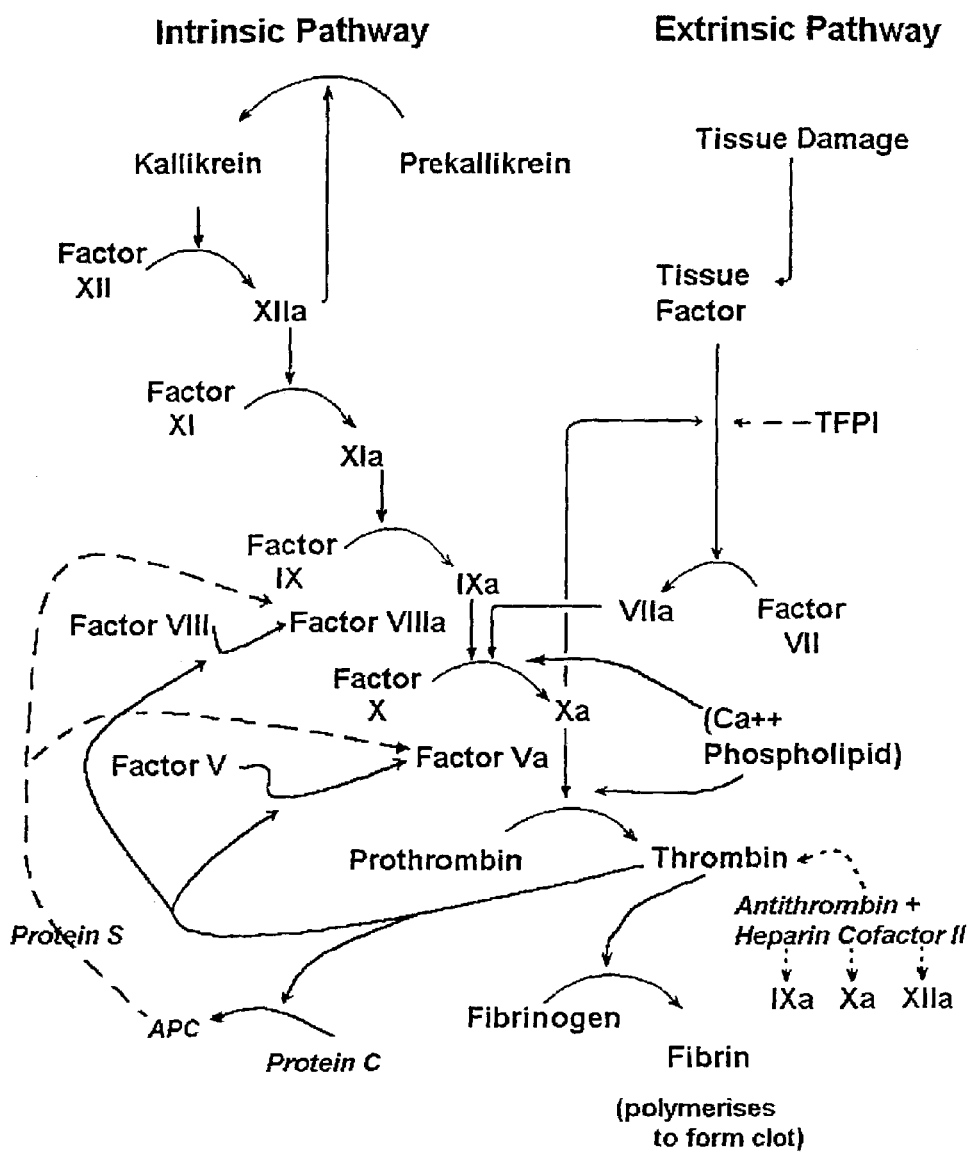
FIG. 1 is a diagram (described above) illustrating the blood coagulation cascade.
Figure 4:
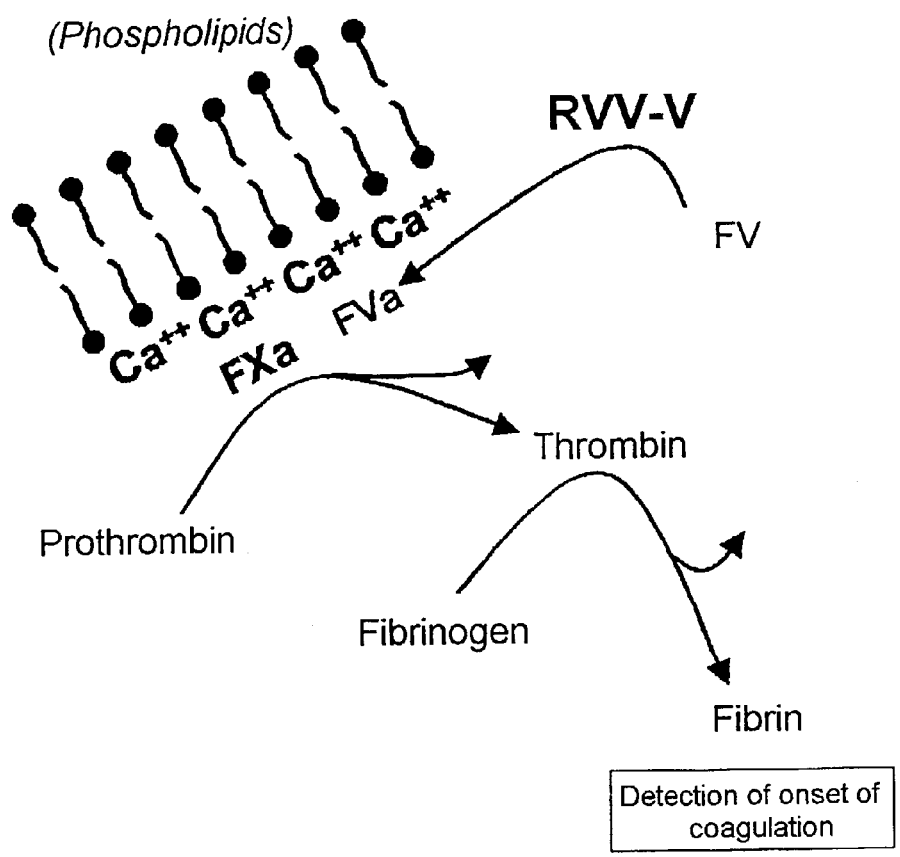
FIG. 4 is a diagram illustrating the principle of the present assay.

In the preferred method of performing the assay, a blood or plasma sample (from which calcium ions are absent or have been complexed or bound e.g by citration) is incubated with a defined amount of factor Xa, phospholipids and factor V-activating enzyme, preferably using a specially prepared activator reagent. After an incubation period the sample/reagent mixture is re-calcified, e.g. with $CaCl_2$ and the time to the onset of clotting (clotting time) is observed and recorded. By comparison with FIG. 1, FIG. 4 illustrates the activation procedure diagrammatically. Components of the activator reagent are shown in large bold letters. Activation relies on the establishment of a prothrombinase complex, consisting of a predetermined amount of factor Xa, patient-own factor V activated using a predetermined amount of factor V-activator from Russell's Viper venom (RVV-V), phospholipids and $CaCl_2$. Re-calcification of citrated blood or plasma is employed to complete the assembly of the prothrombinase complex on the phospholipid surface and clotting begins.

By contrast to previous methods such as the Yin assay in which factor Va is generated by positive feedback activation when thrombin is formed, the inventive method employs a thrombin independent step for immediate complete activation of factor V of the sample to Va. In a modification, excess factor V and/or other factors can be added in order to make the test system independent from changes in the activity of this factor. The added factors can be simply plasma or a plasma fraction. Purified or recombinant factors can be used or suitable mutations.

EXAMPLE 1

Preparation of the Activation Reagent

An activator reagent was prepared having the following composition:

| | |
|---|---|
| NaCl in aqueous solution | 0.9% w/v |
| Tris/HCl buffer, pH 7.4[1] | 50 mM |
| albumin[2] | 0.5% w/v |
| factor Xa (FXa)[3] | 0.4 nkat/ml |
| Russell's Viper venom factor V activator (RVV-V)[4] | 4 U/ml |
| phospholipids[5] | 50 μg/ml |

Assay Procedure

50 μl citrated, platelet-poor plasma were mixed with 50 μl of the activator reagent and various amounts of the anti-clotting agents LMWH[6], UFH[7] and r-hirudin[8] to form test samples. The samples were incubated for 180 seconds at 37° C. 50 μl of 25 mM $CaCl_2$ solution were then added to each sample and the time to clotting measured on a BCS (Dade-Behring) optical coagulometer. The results in terms of anti-coagulant concentration are shown in FIG. 5.

Figure 5:
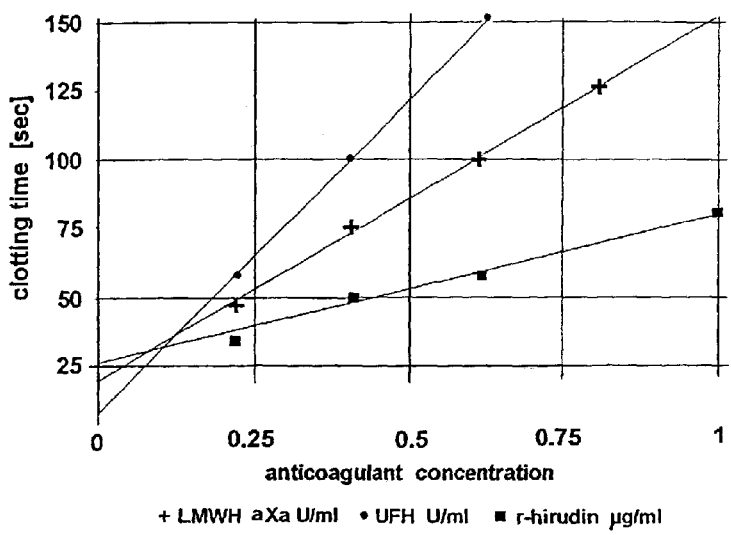
FIG. 5 is a graph similar to FIG. 2 illustrating typical dose response lines for LMWH, UFH and hirudin in an assay according to the invention.

Comparison of FIG. 5 with FIG. 2 shows a great improvement in sensitivity (approaching a factor of 2) over the Heptest®. By contrast to the Heptest® the inventive assay is also very sensitive for hirudin.

Figure 6:
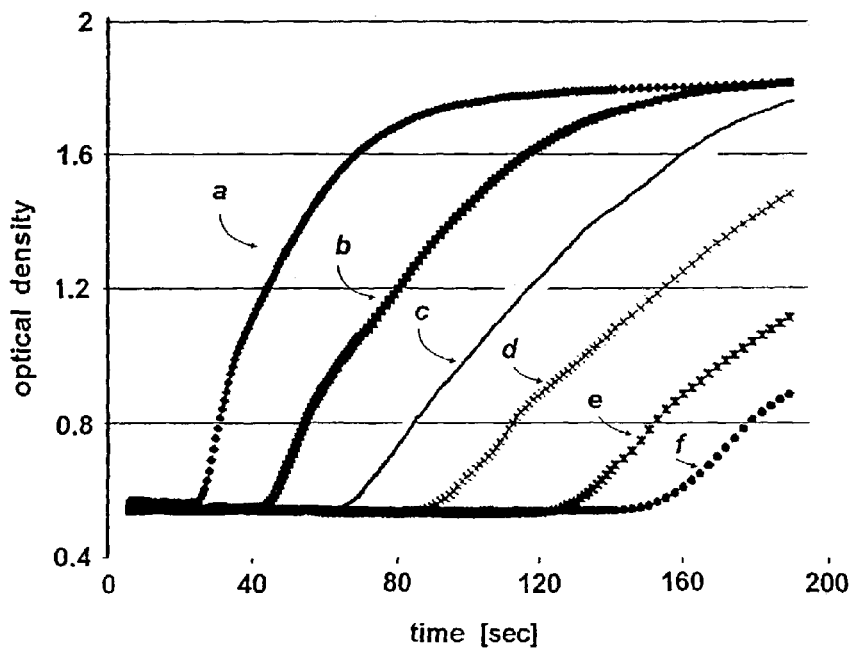
FIG. 6 is a graph similar to FIG. 3 showing optical signal curves produced in an assay according to the invention.

The optical signals for the assay are shown in FIG. 6. A very stable baseline is exhibited at about 405 nm on the Behring Coagulation System by comparison with FIG. 3 and there is a sharp increase in turbidity at the onset of clotting. The signals are very conclusive and display a low noise level. It can therefore be expected that the assay can easily be adapted to different instruments with optical or mechanical detection of the onset of coagulation.

1 from Sigma, Munich
2 human serum albumin from Centeon, Marburg
3 FXa supplied by Chromogenix, Essen
4 from Pentapharm AG, Basel
5 rabbit brain cephalin from Pentapharm AG, Basel
6 WHO standard LMWH from Chromogenix, Essen
7 unfractionated heparin from B. Braun-Melsungen, Melsungen
8 recombinant hirudin (Lepirudin® from Hoechst Marrion Roussel, Bad Soden)

Reference plasma was obtained from Immuno, Vienna and reconstituted as instructed.

EXAMPLE 2

Variation of Factor Xa Concentration

It was unexpectedly found that by varying the added factor Xa concentration, the sensitivity of the activation procedure could be adjusted over a wide range.

Procedure

Figure 7:
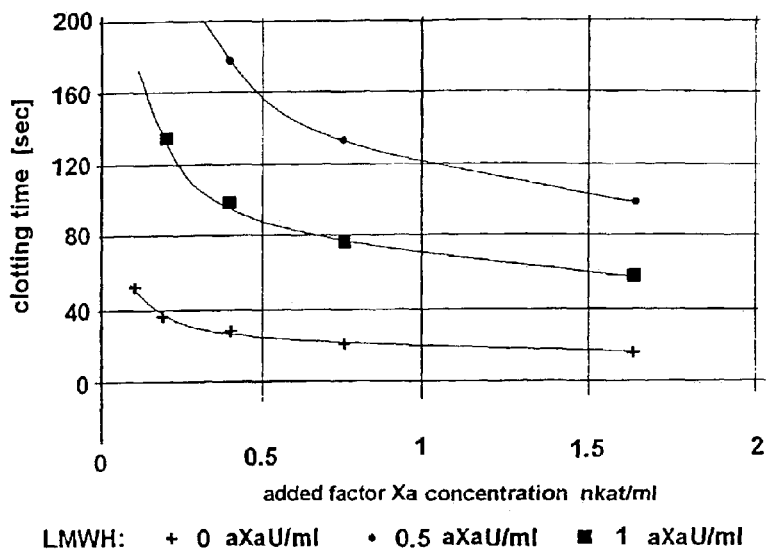
FIG. 7 is a graph illustrating the effect produced by adding additional amounts of factor Xa.

The procedure of Example 1 was followed with the exception that activating reagents with different concentrations of factor Xa (FXa) from 0.1 to 1.6 nkat/ml were prepared and test samples prepared with 0, 0.5 and 1 U/ml of LMWH. The results are shown in FIG. 7. It can be seen that unexpectedly good signals were obtained even with reduced concentration of factor Xa and a stable base line achieved even with heparinised samples.

This discovery enables assays to be designed for a broad spectrum of unknown anti-coagulant concentrations, and a variety of different applications are possible, including:

a) Assays for factor Xa and thrombin inactivation by the assessment of thrombin activity using substrates (e.g. chromogenic substrates) which give detectable signals for thrombin.

b) Assays for factor V inactivation by added activated protein C or endogenous protein C activated using appropriate enzymes (e.g. Protac® or thrombin/thrombomodulin).

c) Assays of other unknowns such as activators, inhibitors or substrates which give detectable signals with factor Xa or thrombin.

EXAMPLE 3

Variation of the Incubation Period

It was also found that performing the activation procedure without an incubation step leads to a very extended measuring range, especially for unfractionated heparin, which is useful in assessing high anticoagulant concentrations.

Preparation of the Activation Reagent

The activator reagent of Example 1 was diluted with an equal volume of 0.025 M calcium chloride solution to produce a reagent having the following composition:

| | |
|---|---|
| NaCl in aqueous solution | 0.45% w/v |
| Tris/HCl buffer | 25 mM (pH 7.4) |
| albumin | 0.25% w/v |
| factor Xa (FXa) | 0.2 nkat/ml |
| Russell's Viper venom factor V activator (RVV-V) | 2 U/ml |
| phospholipids | 25 µg/ml |
| $CaCl_2$ | 12.5 mM |

Procedure

Figure 8:
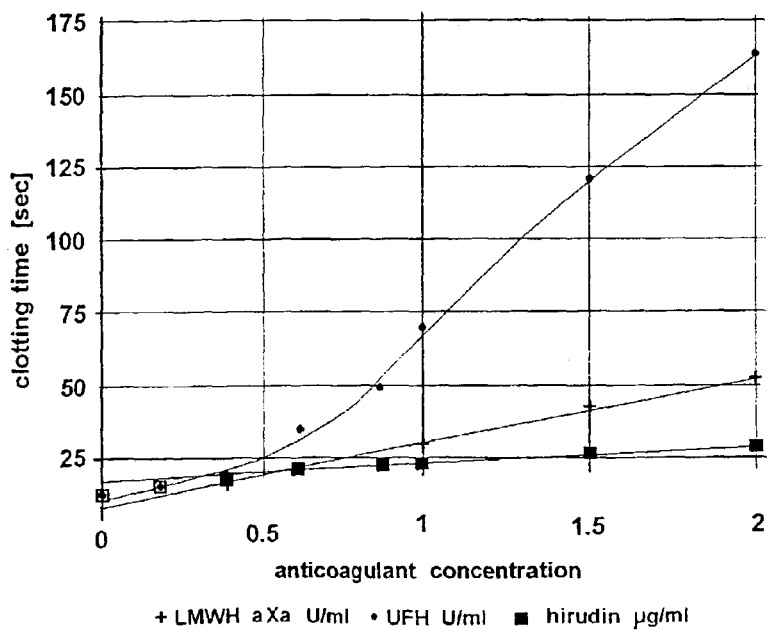
FIG. 8 is a graph illustrating the effect produced by omitting the incubation step.

50 µl test samples of citrated platelet-poor plasma containing varying amounts of LMWH, UFH and r-hirudin were mixed with 100 µl activator reagent and the time to onset of clotting measured as in Example 1. The results shown in FIG. 8 demonstrate a broad measuring range with particularly good results for UFH.

EXAMPLE 4

Patient on Oral Anticoagulant Treatment

Analysis of samples from patients with reduced factor activity following treatment with additional, e.g. oral anticoagulants showed a much lower additive effect of the factor deficiency and anticoagulant in the new assay than in the Heptest® assay. This may be due to the strong direct factor V activation in the new procedure which minimises a potential delay of thrombin mediated factor V activation when thrombin formation is itself retarded due to a reduced factor activity. Thus anticoagulant concentrations can be assessed more reliably using the new assay in such circumstances.

In this example samples were prepared from blood from a patient treated with an oral anticoagulant with an International Normalised Ratio (INR) of 3,2. Presently used oral anticoagulants are coumarin derivatives such as warfarin. These are competitive inhibitors of vitamin K in the gamma-carboxylation of Vitamin K dependent coagulation factors and primarily the respective carboxyproteins lacking in calcium binding capacity are formed. The activity of these factors is reduced.

Figure 9:
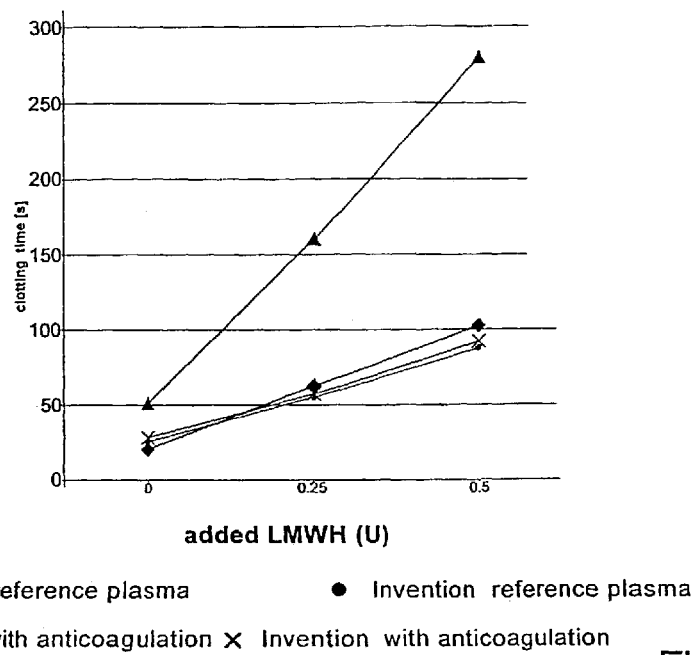
FIG. 9 is a graph illustrating results obtained using the inventive assay and using the Heptest® on a patient treated with an oral anticoagulant.

The samples contained added amounts of 0, 0.25 and 0.5 aXa U LMWH. These samples were subjected to a Heptest® and to the procedure of Example 1. The results are shown graphically in FIG. 9. It will be seen that the oral anticoagulant treatment had little or no effect on the results for LMWH activity in the inventive assay whereas a sharp difference appeared in the Heptest®.

EXAMPLE 5

Use of a Chromogenic Substrate

The following procedure may be used.

50 µl samples of citrate, fresh frozen plasma containing quantities of LMWH, UFH and r-hirudin (as in Example 1) are incubated with 87.4 µl of activator reagent (Example 1) for 5 minutes at 37° C. An accelerant solution is then added containing:

| | |
|---|---|
| Tris/HCl buffer, 50 mM in 0.9% w/v NaCl, pH 7.4 | 562.5 µl |
| Pefabloc(r), 10 mg/ml in 0.9% w/v NaCl | 100 µl |
| $CaCl_2$, 25 mM | 100 µl |
| Chromogenic substrate for thrombin[1], 4 mM in water | 100 µl |

[1]e.g. Tos-Gly-Pro-Arg-pNaAcOH from Pentapharm AG..

The solutions are mixed and the change in optical density measured at 405 nm after incubation for 5 minutes at 37° C.

EXAMPLE 6

Comparison of the Inventive Assay with an Anti-Factor Xa Assay.

Figure 10:
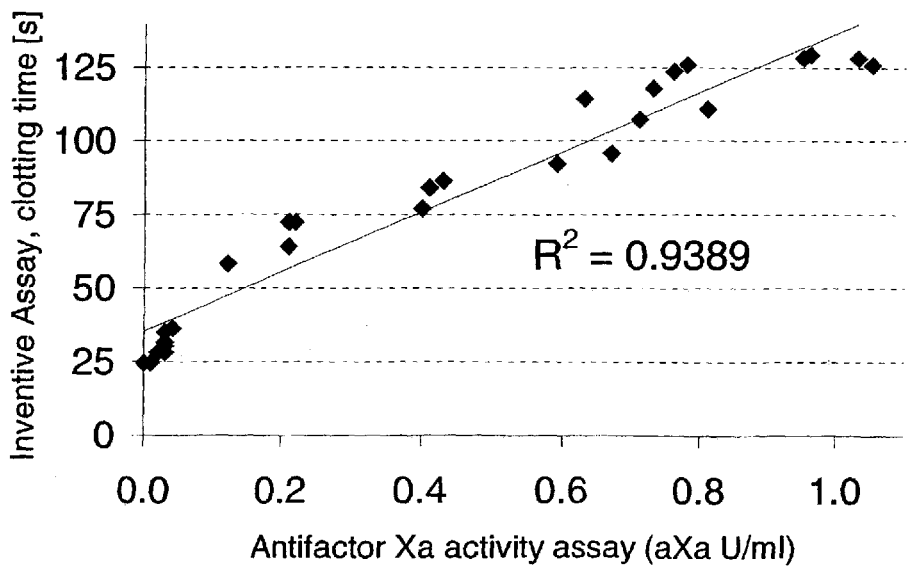
FIG. 10 is a graph showing the correlation of assays according to the invention with assays performed according to the antifactor Xa assay, performed on volunteers treated with LMWH.

The inventive assay was compared to an anti-factor Xa activity assay using a chromogenic substrate. 30 samples taken from volunteers under LMWH treatment were assayed following the procedure of in Example 1 and using the "antifactor Xa activity assay" from Chromogenix, Mölndal, Sweden, following makers instructions. The results, as plotted in FIG. 10, demonstrate a good correlation.

Use of Dry Reagents

The following example illustrates that the activator reagent of the invention can be re-constituted after lyophilisation or air drying in individual samples which can be tested in very small quantities suitable for point-of-care applications.

EXAMPLE 7

Preparation of the Activation Reagent

An activator reagent having the following composition was prepared:

| | |
|---|---|
| NaCl in aqueous solution | 0.9% w/v |
| Tris/HCl buffer, pH 7.4[1] | 50 mM |
| Glycin[2] | 1.0% w/v |
| factor Xa (FXa)[3] | 0.4 nkat/ml |

-continued

| Russell's Viper venom factor V activator (RVV-V)[4] | 4 U/ml |
| --- | --- |
| phospholipids[5] | 50 µg/ml |

1 ml portions were filled in vials and lyophilised or 50 µl of the activator reagent were added to cuvettes for the KC4 Micro Coagulometer and air-dried for 24 h.

Assay Procedure

50 µl of citrated, platelet-poor plasma were mixed with 50 µl of the activator reagent, which was reconstituted in water after lyophilisation and various amounts of the anti-clotting agents LMWH[6], UFH[7] and r-hirudin[8] to form test samples. For comparison 50 µl of water were added to the reagent which had been air-dried in cuvettes, and the samples were mixed with 50 µl of the platelet-poor plasma and various amounts of the same anti-clotting agents LMWH, UFH and r-hirudin to form test samples. The samples were incubated for 180 seconds at 37° C. 50 µl of 25 mM $CaCl_2$ solution were then added to each sample and the time to clotting measured on a KC4 Micro Coagulometer. The results shown in FIGS. 11a–11c in terms of anti-coagulant demonstrate that the assay can easily be performed with reagents that were dried in different ways and slight differences between different drying methods can be seen in the performance of the assays.

1 from Sigma, Buchs, Switzerland
2 from Sigma, Buchs, Switzerland
3 FXa, IL, Milano, Italy
4 RVV-V, from Pentapharm AG, Basel, Switzerland
5 rabbit brain cephalin, Pentapharm Ltd, Basel, Switzerland
6 WHO standard LMWH, NIBSC, Potters Bar, UK
7 WHO standard UH, NIBSC, Potters Bar, UK
8 recombinant hirudin, Pentapharm Ltd, Basel, Switzerland
Reference plasma was obtained from Immuno, Vienna and reconstituted as instructed.

Point-of-Care Applications

In many situations blood coagulation tests have to performed directly at the point of care without transport of the sample to an emergency laboratory. The advantages of point of care analysis include:

Short turn-around time, as there is no time or only little time needed for transport of the sample. This may allow fast monitoring-directed therapeutic decisions.
Transport of a sample to an emergency laboratory can be very expensive, especially at night and when only few samples are to be analyzed.
Self testing by the patient is possible.

Available point of care methods for analysis of anticoagulation include PT (prothrombin time) aPTT (activated partial prothrombin time), ACT (activated clotting time) and related methods as well as some new approaches for heparin testing.

Point-of-care aPTT tests have the same limitations as the determination of aPTT in the laboratory: non-linear dose response for UFH and hirudin, low sensitivity towards LMWH and high variation between the different available methods. PT tests have similar disadvantages.

The ACT basically relies on the addition of a substance with a high negatively charged surface (usually kaolin or celite) to non-anti-coagulated blood. Disadvantages of the ACT include its low precision, low correlation of ACT values towards unfractionated heparin or hirudin concentration, long measuring times as well as the high variation among different commercially available methods. In addition the sensitivity of the ACT towards LMWH is very low.

Another approach is the ACT-based protamine titration: Protamine sulfate antagonizes unfractionated heparin. 1U of unfractionated heparin is antagonized by 1 U of protamine sulfate. If given in excess, protamine itself prolongs the ACT in a concentration-dependent manner. Thus when protamine is added in rising concentrations to ACT determinations and a heparinised sample is analyzed, the shortest clotting times are achieved when the concentration of added protamine corresponds best to the heparin concentration in the sample.

In the protamine titration assay of Medtronic (Bull, M. H. et al Anesthesiology, September 1975, 43(3), 346–353) a cartridge with 6 chambers is provided which contain the ACT activator and different protamine concentrations. In these chambers separate ACT determinations are performed and the heparin concentration is calculated.

Limitations of this method include:

It is only applicable to UFH monitoring (hirudin is not antagonized by protamine, as the assay is based on the ACT, it is not applicable to LMWH monitoring). Multiple determinations are required for the analysis of one sample and several different cartridges are necessary for the monitoring of different concentration ranges of heparin therapy.

A number of publications describe point-of-care testing devices utilising reaction chambers separated by capillaries, so that sample material such as blood or other body fluid passes in a controlled manner to fill chambers of controlled volume which can contain predetermined quantities of reagents. In this way the exact measurement of sample material can be avoided (e.g. U.S. Pat. Nos. 4,756,884, 5,300,779 (Biotrack), 5,110,727 (Cardiovascular).

A considerable bibliography covering use of the CoaguChek[R] device referred to earlier is available from the web site of Roche Diagnostics GmbH. As described in van den Besselaar A. M. H. P., et al., *Multicenter evaluation of a new capillary blood prothrombin time monitoring system* Blood Coagulation and Fibrinolysis 1995, 6, 726–732, the device uses a test carrier resembling FIG. 11 of U.S. Pat. No. 5,110,727. For use in a PT assay the carrier (which is described by reference in Oberhardt B. J. et. al., *Dry reagent technology for rapid convenient measurements of blood coagulation and fibrinolysis,* Clin. Chem. 1991, 37, 520–526) contains iron oxide particles mixed with dry rabbit brain thromboplastin in a reaction chamber (or "reaction zone") connected to an open inlet chamber (or "sample application zone") via a capillary. A blood sample from a pierced finger is applied to the inlet chamber whence the blood is drawn by capillary forces into the reaction chamber. Contact with the thromboplastin then triggers the coagulation cascade. The iron oxide particles are forced to align vertically by magnets, one of which causes pulsing. A photocell registers the pulsing pattern which reduces and finally ceases upon formation of the fibrin matrix. Similar devices on the market include the TAS[R] (Thrombolytic Assessment System) analyser of Cardiovascular Diagnostics Inc., the Coumatrak[R] device of Biotrack Inc., and the Coag-A-Mate[R] device of Organon Teknika Inc.

In conclusion there is no simple universal monitoring assay available for the analysis of UFH LMWH and hirudin at the point of care.

We have found that by activating coagulation in accordance with the method of the invention, e.g. with a combination of FXa and an enzyme activating FV such as RVV-V, improved assays for point-of-care analysis of anticoagulants can be designed. These assays can also be directly performed on whole blood, so no centrifugation step is required.

Thus the invention is inclusive of a point-of-care hematological assay wherein a sample of activator reagent as described above is positioned in one or more reaction locations in a test apparatus and a sample of body fluid to be assayed (e.g. whole blood or citrated blood) is applied at an inlet location (e.g. an open chamber) in said apparatus and arranged to contact and react with the activator reagent, e.g. via a capillary, and a value is established indicative of the coagulation potential of the body fluid.

Preferably the activator reagent is in a dry (preferably lyophilised) condition and is dissolved by the said body fluid to form an aqueous solution.

Preferably a said reaction location is defined by a reaction chamber of predetermined volume and the sample of activator reagent is of predetermined weight so as to form with the body fluid an aqueous solution of predetermined concentration.

The said test apparatus may comprise two or more reaction chambers interconnected e.g. by capillaries, the said body fluid being arranged to react successively with reagents in the respective chambers. Thus the said body fluid may react with FXa and RVV-V in a first reaction chamber and with $CaCl_2$ (or equivalent salt) in a second reaction chamber.

The reagents are preferably dried in situ by lyophilisation. However room temperature air drying, vacuum drying, desiccant drying, convective drying or other drying method may be used. Coating of the dry reagents on the chamber walls reduces displacement by shaking, but is not essential. The dry or aqueous reagents may be located on matrices such as sponge or fleece material or may be microencapsulated. Although the two essential components of the activator reagent are preferably located together, they could in an equivalent manner be located in separate chambers through which the sample passes in succession.

The following examples refer to FIGS. 12 and 13 which show capillary testing devices in diagrammatic form. For methods of manufacturing such devices reference may be made to the aforementioned U.S. Pat. Nos. 4,756,884, 5,110,727 and 5,300,779, e.g. FIG. 2a of U.S. Pat. No. 5,300,779.

EXAMPLE 8

Untreated Whole Blood

A non-anticoagulated freshly drawn whole blood sample is placed in the inlet chamber 1 of the capillary testing device shown in FIG. 12. Sufficient blood is drawn along capillary 3 into the reagent chamber 2 by capillary forces to fill the chamber. The amount of blood that is contacted by the reagents is standardized by the size of the reagent chamber without the need for exact dispensing of the sample. Chamber 2 is coated with activating reagent comprising FXa and RVV-V in a dry, preferably lyophilised state. Here the blood sample dissolves the reagent and is activated. Clotting can be detected by optical means at the site of chamber 2 or at a point along the outlet capillary 4, optionally with the addition to the activating reagent of accessory agents such as chromogenic substrates, fluorogenic substrates, amperogenic substrates, and paramagnetic particles. By varying the added FXa concentration the sensitivity and measuring range can be set as required.

The reaction leading to clotting of the sample involves inhibition of the added FXa by antithrombin alone, antithrombin-UFH or antithrombin-LMWH complexes, activation of FV by the added RVV-V, formation of the prothrombinase complex on endogenous phospholipid structures (especially the platelet surfaces) and then formation of free thrombin. While these reactions occur in the fluid state, the reagents may be placed in the reagent chamber in liquid or in dry form. Where the reagents are placed in the chamber in dry form, the reagents are dissolved by the sample. This can be facilitated by adding substances to the reagent prior to lyophilisation or other drying process. The main advantage of the use of dry reagents may be a longer stability of the cartridge when compared to liquid reagents. However, when liquid reagents are used, stability can be optimized by buffering the reagents to an appropriate pH. When the sample is added, the buffering capacity of the sample returns the reagent to the optimal pH near 7.4. By using a low buffering capacity, e.g. 2 mM, for the reagent the buffering capacity of the sample itself can easily correct the pH for the reaction.

EXAMPLE 9

Citrated Blood Sample, One-Step Reaction

A combination of FXa, RVV-V and $CaCl_2$ is placed in reagent chamber 2 of FIG. 12, preferably in a dry state, e.g. lyophilised, and a sample of citrated blood is inserted into inlet chamber 1. After entering chamber 2 along capillary 3, the sample is simultaneously re-calcified as it contacts and dissolves the FXa and RVV-V. Clotting can be detected as in Example 8. In order to reduce the sensitivity of the assay and thus in order to enhance the measuring range it is possible to add phospholipids to the reagent mixture. In this case complexes of phospholipids and FXa are formed in the reagent (mediated by free calcium ions), which reduce the ability of antithrombin in the sample to inhibit the added FXa. This can be applied to the design of point-of-care tests for very high amounts of heparin, e.g. for application in the monitoring of heparin therapy during open heart surgery.

EXAMPLE 10

Citrated Blood Sample, Two-Step Reaction

A citrated blood sample is transferred to the inlet chamber 1a of the device of FIG. 13. The sample material moves under capillary forces along the capillary 5 to chamber 2a which is coated with dried FXa and RVV-V Activated sample material is drawn by capillary forces into chamber 3 which is coated with dried $CaCl_2$. In reagent chamber 3 the sample is re-calcified by contact with the $CaCl_2$. In this example the concentration is more standardised as a more defined volume of sample contacts the reagents. The incubation time of the sample with FXa and RVV-V depends on the length of the capillary 6 connecting the two reagent chambers and on the velocity of the sample/reagent mixture through this capillary, which depends on the diameter of the capillary. Incubation of the citrated sample with FXa and RVV-V in the absence of free calcium ions results in a higher sensitivity of the assay towards anti-factor-Xa activity than in the two previous examples. This relies on the fact that FXa is protected against inhibition by antithrombin when it is associated to phospholipid surfaces including platelets. The association of FXa to phospholipid surfaces is mediated by free calcium ions and by the carboxyl groups in the FXa molecules which are dependent on Vitamin K during the biosynthesis of the molecule in the liver. In the absence of free calcium ions, the FXa molecules can be inhibited by antithrombin-heparin complexes. By the length of the capillary 6 between the two reagent chambers, the sensitivity of the assay towards anti-Xa activity can be adjusted as required.

Variations

The present activator reagent and activation procedure gives rise to numerous variations in assays and in other applications. In particular the procedure may be varied to assay an unknown sample of one of the ingredients described. Some variations are illustrated below.

1. Variations Involving the Detection of the Onset of Coagulation i) Thrombin formation may be detected by the addition of a synthetic substrate known for this purpose. The substrate may have chromogenic, fluorogenic, amperogenic, luminogenic or other measurable property. The substrate may for example be cleaved by thrombin to leave a detectable group.

ii) Known detection methods may be used for measuring viscosity, elasticity, flow characteristics, clot resonance, the movement of erythrocytes or the behaviour of added objects such as particles which alter their behaviour upon the onset of coagulation. For example the oscillation of added magnetic particles may be measured or the mechanical characteristics of added particles.

iii) Rapid immunological detection procedures with thrombin specific antibodies may be applied, e.g. in conjunction with plasmon resonance or similar techniques.

2. Variations Involving Factor Xa

Instead of adding a defined amount of factor Xa from bovine, human or other origin to the sample a substance which activates endogenous factor Xa could be used, or a substance with a similar function to factor Xa, e.g. mutants of factor Xa, snake venom enzymes, or factor Xa-activating cysteine proteinase from tumor cells.

3. Variations Involving Factor V

Instead of activating endogenous factor V in plasma or other source by the addition of RVV-V or factor V activators from other snake venoms such as Akgistrodon species, Bothrops species, *Vipera lebetina,* Echis species or alternative activating substance, certain applications may employ already activated factor V or a substance with a similar function to factor V, e.g. a mutant of factor V.

4. Variations Involving Phospholipids

Certain applications may employ other sources of phospholipids, e.g.:

i) The contribution of the patient's own phospholipid structures to coagulation may be assessed, e.g. by using a sample in which platelets are present.

ii) Phospholipids may be assayed by using a two step procedure in which in one of the steps the unknown phospholipid is added.

iii) The concentration of phospholipids can be adjusted in order to minimise where necessary the potential interference of lupus anticoagulants or anti-phospholipid antibodies.

The phospholipids may be of human, animal, plant or synthetic origin or a mixture of such.

5. Variations Involving Anticoagulants

The assay procedure can be made specific to heparin-independent inhibitors of factor X, II or V by the addition of substances which inactivate heparin, e.g. protamine, heparinase or polybren.

6. Variations Involving Plasma

The procedure may be performed with the addition of plasma, plasma fractions or single factors in order to correct factor deficiencies or in order to make the test more susceptible or less susceptible to certain mechanisms. Such added substance may include e.g.:

i) Human normal plasma or plasma fractions or single factors or similar mutants.

ii) Bovine (or other animal) normal plasma or plasma fractions or single factors or similar mutants.

7. Variations Involving Other Factors

The procedure may be performed with the addition of synthetic substrates, activators or inhibitors of any one or selected combination of factors II, IIa, V, Va, X and Xa.

CONCLUSION

In conclusion, the present invention includes a simple plasma clotting assay based on defined, readily available and easy to stabilise components. The results show linear dose-response relationships for LMWH, hirudin and UFH. These very good dose-response relationships appear to rely on the assessment of anti-factor IIa and anti-factor Xa activity independently of earlier stages of the coagulation cascade and independently of factor V activation during the initiation of coagulation by thrombin generated from the samples' coagulation factors.

In contrast to techniques which activate prothrombin by prothrombin activators from snake venoms (e.g. the ECT method for hirudin determination), the present technique uses the physiological pathway of prothrombin activation (using factor Xa, factor Va, phospholipids and calcium ions), which is of advantage for the assessment of physiologically relevant coagulation mechanisms and processes.

The good optical signal, high precision, short measuring times and the ease of performance using the standard procedures of the aPTT and PT allow adaptability of the new procedure to different coagulation analysers.

Comparison of the results of the new procedure, based on preformed prothrombinase, and the Heptest® which employs factor Xa only, prior to incubation, shows that the two tests present significant differences. The Heptest® had longer coagulation times with the LMWH samples when compared to the inventive assay, and its sensitivity was slightly lower for UFH and dramatically lower for hirudin. Compared to the Heptest® the new method works on a defined physiological basis, does not require bovine plasma fraction, activates factor V independently from thrombin, has an improved optical signal and shows high sensitivity to hirudin. Therefore it can be used to monitor not only UFH and LMWH but also hirudin with the same reagent in relevant concentration ranges.

By contrast to the invention, the Russell's Viper venom time assay employs both factor V and factor X activation by the venom, which results in varying factor Xa concentrations depending on the patient's factor X concentration. A more defined activation is achieved in the invention by the application of a defined factor Xa activity.

Finally, the invention provides a procedure which allows a simple assay for the monitoring of LMWH, heparinoids, hirudins and UFH based on a single principle. A variety of further tests are possible when the activation regimen is combined with substances which activate or inhibit processes which affect factor V, X or II directly or indirectly (like the protein C system), or the use of indicator substrates.

What is claimed is:

1. A method of determining the blood coagulation potential of a body fluid selected from whole blood, citrated or equivalently stabilized blood, and plasma, comprising:
   (i) contacting an activator reagent with a sample of the body fluid, wherein the reagent reacts with the body fluid, said reagent comprising:
   (a) a predetermined amount of factor Xa or a hematologically equivalent mutant thereof; and
   (b) a predetermined amount of factor Va, a hematologically equivalent mutant thereof, or an enzyme which activates endogenous factor V;
   (ii) if necessary, inducing coagulation by adding one or more coagulation accelerants; and
   (iii) establishing a value indicative of the coagulation potential,
   wherein the establishment of the value indicative of the coagulation potential comprises measuring one of the following:
   (a) the time between the contacting of the activation reagent with or without the coagulation accelerant to said sample and the onset of clotting;
   (b) the time between the addition of said reagent with or without the coagulation accelerant to said sample and the detection of free thrombin activity;
   (c) the thrombin activity; and
   (d) the factor Xa activity,
   and wherein the time between the addition of said reagent with or without the coagulation accelerant to said sample and the onset of clotting is measured using an optical coagulometer.

2. A method of determining the blood coagulation potential of a body fluid selected from whole blood, citrated or equivalently stabilized blood, and plasma, comprising:
   (i) contacting an activator reagent with a sample of the body fluid, wherein the reagent reacts with the body fluid, said reagent comprising:
   (a) a predetermined amount of factor Xa or a hematologically equivalent mutant thereof; and
   (b) a predetermined amount of factor Va, a hematologically equivalent mutant thereof, or an enzyme which activates endogenous factor V;
   (ii) if necessary, inducing coagulation by adding one or more coagulation accelerants; and
   (iii) establishing a value indicative of the coagulation potential,
   wherein the establishment of the value indicative of the coagulation potential comprises measuring one of the following:
   (a) the time between the contacting of the activation reagent with or without the coagulation accelerant to said sample and the onset of clotting;
   (b) the time between the addition of said reagent with or without the coagulation accelerant to said sample and the detection of free thrombin activity;
   (c) the thrombin activity; and
   (d) the factor Xa activity,
   and wherein the value indicative of the coagulation potential is established by adding to the reaction mixture an analytical accessory agent which provides a detectable value, wherein the analytical accessory agent is a particle exhibiting during coagulation mechanical, magnetic or electrical activity corresponding to the thrombin activity or factor Xa activity.

3. A method of determining coagulation potential of a citrated platelet-poor plasma comprising:
   (i) preparing an activator reagent comprising:
   (a) 0.2 nkat/ml factor Xa;
   (b) 2 U/ml RVV-V; and
   (c) 25 $\mu$g/ml phospholipids from rabbit brain cephalin, in an aqueous buffer solution containing 25 mM Tris/HCl, 0.45% w/v NaCl, 0.25% w/v albumin and 12.5 mM $CaCl_2$, at pH 7.4;
   (ii) mixing 50 $\mu$l of the citrated platelet-poor plasma with 100 $\mu$l of the activator reagent;
   (iii) optionally adding an analytical accessory agent providing a detectable value; and
   (iv) establishing the value indicative of the coagulation potential.

4. The method according to claim 3, wherein the value indicative of the coagulation potential is established by measuring with an optical coagulometer the time between the addition of $CaCl_2$ and the onset of clotting.

5. A method of determining the blood coagulation potential of a body fluid selected from whole blood, citrated or equivalently stabilized blood, and plasma, comprising:
   (i) contacting an activator reagent with a sample of the body fluid, wherein the reagent reacts with the body fluid, said reagent comprising:
   (a) a predetermined amount of factor Xa or a hematologically equivalent mutant thereof; and
   (b) a predetermined amount of factor Va, a hematologically equivalent mutant thereof, or an enzyme which activates endogenous factor V;
   (ii) if necessary, inducing coagulation by adding one or more coagulation accelerants; and
   (iii) establishing a value indicative of the coagulation potential,
   and further comprising incubating the sample reacted with the activator reagent; and then adding to the reaction mixture the accelerator and optionally an analytical accessory agent, wherein the method further comprises:
   (i) preparing an activator reagent comprising:
   (a) a predetermined amount from 0.01 to 10 nkat/ml of factor Xa;
   (b) a predetermined amount from 0.05 to 10 U/ml of RVV-V; and
   (c) optionally a predetermined amount from 1 to 200 $\mu$g/ml of phospholipids,
   in an aqueous buffer solution containing from 10 to 200 mM Tris/HCl, from 0.6 to 1.2% w/v NaCl, and from 0.01 to 1.0% w/v albumin;
   (ii) mixing a predetermined amount from 1 to 100 $\mu$l of the sample with a predetermined amount from 1 to 100 $\mu$l of the activator reagent, wherein the sample is citrated or equivalently stabilized platelet-poor plasma;
   (iii) incubating the mixture;
   (iv) adding a predetermined amount from 10 to 100 $\mu$l of from 2 to 200 mM $CaCl_2$;
   (v) optionally adding an analytical accessory agent providing a detectable value; and
   (vi) establishing the value indicative of the coagulation potential.

6. A method according to claim 5 comprising:
   (i) preparing an activator reagent comprising:
   (a) 0.4 nkat/ml of factor Xa;
   (b) 4 U/ml of RVV-V; and
   (c) 50 $\mu$g/ml phospholipids from rabbit brain cephalin;

in an aqueous buffer solution containing 50 mM Tris/HCl, 0.9% w/v NaCl and 0.5% w/v albumin at pH 7.4;
(ii) mixing 50 µl of citrated platelet-poor plasma with 50 µl of the activator reagent;
(iii) incubating the mixture for 3 minutes at 37° C.;
(iv) adding 50 µl of 25 mM $CaCl_2$;
(v) optionally adding an analytical accessory agent providing a detectable value; and
(vi) establishing the value indicative of the coagulation potential.

7. The method according to claim 6, wherein the value is established by measuring using optical coagulometer the time between the addition of $CaCl_2$ and the onset of clotting.

8. The method according to claim 5, wherein the value is established by measuring using optical coagulometer the time between the addition of $CaCl_2$ and the onset of clotting.

9. A method of determining the blood coagulation potential of a body fluid selected from whole blood, citrated or equivalently stabilized blood, and plasma, comprising:
(i) contacting an activator reagent with a sample of the body fluid, wherein the reagent reacts with the body fluid, said reagent comprising:
(a) a predetermined amount of factor Xa or a hematologically equivalent mutant thereof; and
(b) a predetermined amount of factor Va, a hematologically equivalent mutant thereof, or an enzyme which activates endogenous factor V;
(ii) if necessary, inducing coagulation by adding one or more coagulation accelerants; and
(iii) establishing a value indicative of the coagulation potential,
and further comprising:
(i) preparing an activator reagent comprising:
(a) a predetermined amount from 0.01 to 10 nkat/ml of factor Xa;
(b) a predetermined amount from 0.05 to 10 U/ml of RVV-V; and
(c) optionally a predetermined amount from 1 to 200 µg/ml of phospholipids,
in an aqueous buffer solution containing from 10 to 200 mM Tris/HCl, from 0.6 to 1.2% w/v NaCl, and from 0.01 to 1.0% w/v albumin;
(ii) mixing a predetermined amount from 1 to 100 µl of the sample with a predetermined amount from 1 to 100 µl of the activator reagent, wherein the sample is citrated or equivalently stabilized platelet-poor plasma;
(iii) adding a predetermined amount from 10 to 100 µl of from 2 to 200 mM $CaCl_2$;
(iv) optionally adding an analytical accessory agent providing a detectable value; and
(v) establishing the value indicative of the coagulation potential.

10. A method according to claim 9 comprising:
(i) preparing an activator reagent comprising:
(a) 0.4 nkat/ml of factor Xa;
(b) 4 U/ml of RVV-V; and
(c) 50 µg/ml phospholipids from rabbit brain cephalin;
in an aqueous buffer solution containing 50 mM Tris/HCl, 0.9% w/v NaCl and 0.5% w/v albumin at pH 7.4;
(ii) mixing 50 µl of citrated platelet-poor plasma with 50 µl of the activator reagent;
(iii) adding 50 µl of 25 mM $CaCl_2$;
(iv) optionally adding an analytical accessory agent providing a detectable value; and
(v) establishing the value indicative of the coagulation potential.

11. The method according to claim 10, wherein the value is established by measuring using optical coagulometer the time between the addition of $CaCl_2$ and the onset of clotting.

12. The method according to claim 9, wherein the value is established by measuring using optical coagulometer the time between the addition of $CaCl_2$ and the onset of clotting.

13. A method of determining a blood coagulation component or treatment additive in a sample containing a predetermined amount of human body fluid, comprising comparing the coagulation potential of the sample with that of a comparable normal human body fluid and/or that of a comparable human body fluid which either lacks the component or additive, or contains a known amount of the component or additive in excess, wherein coagulation potential is determined by a method comprising:
(i) contacting an activator reagent with a sample of the body fluid, wherein the reagent reacts with the body fluid, said reagent comprising:
(a) a predetermined amount of factor Xa or a hematologically equivalent mutant thereof; and
(b) a predetermined amount of factor Va, a hematologically equivalent mutant thereof, or an enzyme which activates endogenous factor V;
(ii) if necessary, inducing coagulation by adding one or more coagulation accelerants; and
(iii) establishing a value indicative of the coagulation potential,
said method further comprising:
(i) preparing an activator reagent comprising:
(a) a predetermined amount from 0.01 to 10 nkat/ml of factor Xa;
(b) a predetermined amount from 0.05 to 10 U/ml of RVV-V; and
(c) optionally a predetermined amount from 1 to 200 µg/ml of phospholipids,
in an aqueous buffer solution containing from 10 to 200 mM Tris/HCl, from 0.6 to 1.2% w/v NaCl, and from 0.01 to 1.0% w/v albumin;
(ii) mixing a predetermined amount from 1 to 100 µl of the sample with a predetermined amount from 1 to 100 µl of the activator reagent, wherein the sample is citrated or equivalently stabilized platelet-poor plasma;
(iii) incubating the mixture;
(iv) adding a predetermined amount from 10 to 100 µl of from 2 to 200 mM $CaCl_2$;
(v) optionally adding an analytical accessory agent providing a detectable value; and
(vi) establishing the value indicative of the coagulation potential.

14. A method according to claim 13 comprising:
(i) preparing an activator reagent comprising:
(a) 0.4 nkat/ml of factor Xa;
(b) 4 U/ml of RVV-V; and
(c) 50 µg/ml phospholipids from rabbit brain cephalin;
in an aqueous buffer solution containing 50 mM Tris/HCl, 0.9% w/v NaCl and 0.5% w/v albumin at pH 7.4;
(ii) mixing 50 µl of citrated platelet-poor plasma with 50 µl of the activator reagent;
(iii) incubating the mixture for 3 minutes at 37° C.;
(iv) adding 50 µl of 25 mM $CaCl_2$;
(v) optionally adding an analytical accessory agent providing a detectable value; and
(vi) establishing the value indicative of the coagulation potential.

15. The method according to claim 14, wherein the value is established by measuring using optical coagulometer the time between the addition of $CaCl_2$ and the onset of clotting.

16. The method according to claim 13, wherein the value is established by measuring using optical coagulometer the time between the addition of $CaCl_2$ and the onset of clotting.

17. A method of determining a blood coagulation component or treatment additive in a sample containing a predetermined amount of human body fluid, comprising comparing the coagulation potential of the sample with that of a comparable normal human body fluid and/or that of a comparable human body fluid which either lacks the component or additive, or contains a known amount of the component or additive in excess, wherein coagulation potential is determined by a method comprising:
(i) contacting an activator reagent with a sample of the body fluid, wherein the reagent reacts with the body fluid, said reagent comprising:
(a) a predetermined amount of factor Xa or a hematologically equivalent mutant thereof; and
(b) a predetermined amount of factor Va, a hematologically equivalent mutant thereof, or an enzyme which activates endogenous factor V;
(ii) if necessary, inducing coagulation by adding one or more coagulation accelerants; and
(iii) establishing a value indicative of the coagulation potential,
and further comprising:
(i) preparing an activator reagent comprising:
(a) a predetermined amount from 0.01 to 10 nkat/ml of factor Xa;
(b) a predetermined amount from 0.05 to 10 U/ml of RVV-V; and
(c) optionally a predetermined amount from 1 to 200 µg/ml of phospholipids,
in an aqueous buffer solution containing from 10 to 200 mM Tris/HCl, from 0.6 to 1.2% w/v NaCl, and from 0.01 to 1.0% w/v albumin;
(ii) mixing a predetermined amount from 1 to 100 µl of the sample with a predetermined amount from 1 to 100 µl of the activator reagent, wherein the sample is citrated or equivalently stabilized platelet-poor plasma;
(iii) adding a predetermined amount from 10 to 100 µl of from 2 to 200 mM $CaCl_2$;
(iv) optionally adding an analytical accessory agent providing a detectable value; and
(v) establishing the value indicative of the coagulation potential.

18. A method according to claim 17 comprising:
(i) preparing an activator reagent comprising:
(a) 0.4 nkat/ml of factor Xa;
(b) 4 U/ml of RVV-V; and
(c) 50 µg/ml phospholipids from rabbit brain cephalin;
in an aqueous buffer solution containing 50 mM Tris/HCl, 0.9% w/v NaCl and 0.5% w/v albumin at pH 7.4;
(ii) mixing 50 µl of citrated platelet-poor plasma with 50 µl of the activator reagent;
(iii) adding 50 µl of 25 mM $CaCl_2$;
(iv) optionally adding an analytical accessory agent providing a detectable value; and
(v) establishing the value indicative of the coagulation potential.

19. The method according to claim 18, wherein the value is established by measuring using optical coagulometer the time between the addition of $CaCl_2$ and the onset of clotting.

20. The method according to claim 17, wherein the value is established by measuring using optical coagulometer the time between the addition of $CaCl_2$ and the onset of clotting.

21. The method of determining the blood coagulation potential of a body fluid selected from whole blood, citrated or equivalently stabilized blood, and plasma, comprising:
(i) contacting an activator reagent with a sample of the body fluid, wherein the reagent reacts with the body fluid, said reagent comprising:
(a) a predetermined amount of factor Xa or a hematologically equivalent mutant thereof; and
(b) a predetermined amount of factor Va, a hematologically equivalent mutant thereof, or an enzyme which activates endogenous factor V;
(ii) if necessary, inducing coagulation by adding one or more coagulation accelerants; and
(iii) establishing a value indicative of the coagulation potential,
wherein the sample is diluted in plasma depleted only of a coagulant or anticoagulant component which is suspected to be present in the sample and the established value indicative of the coagulation potential is compared with that of the depleted plasma and/or normal plasma.

22. A method of determining the blood coagulation potential of a body fluid selected from whole blood, citrated or equivalently stabilized blood, and plasma, comprising:
(i) contacting an activator reagent with a sample of the body fluid, wherein the reagent reacts with the body fluid, said reagent comprising:
(a) a predetermined amount of factor Xa or a hematologically equivalent mutant thereof; and
(b) a predetermined amount of factor Va, a hematologically equivalent mutant thereof, or an enzyme which activates endogenous factor V;
(ii) if necessary, inducing coagulation by adding one or more coagulation accelerants; and
(iii) establishing a value indicative of the coagulation potential,
wherein the sample is diluted in normal plasma, a plasma fraction or one or more coagulation factors to reduce the influence of matrix effects.

23. A method of determining the blood coagulation potential of a body fluid selected from whole blood, citrated or equivalently stabilized blood, and plasma, comprising:
(i) contacting an activator reagent with a sample of the body fluid, wherein the reagent reacts with the body fluid, said reagent comprising:
(a) a predetermined amount of factor Xa or a hematologically equivalent mutant thereof; and
(b) a predetermined amount of factor Va, a hematologically equivalent mutant thereof, or an enzyme which activates endogenous factor V;
(ii) if necessary, inducing coagulation by adding one or more coagulation accelerants; and
(iii) establishing a value indicative of the coagulation potential,
wherein the sample is treated with a substance which inactivates heparin or heparin-like substances thereby enhancing specificity to non-heparin anticoagulants.

24. A method of determining a blood coagulation component or treatment additive in a sample containing a predetermined amount of human body fluid, comprising comparing the coagulation potential of the sample with that of a comparable normal human body fluid and/or that of a comparable human body fluid which either lacks the component or additive, or contains a known amount of the component or additive in excess, wherein coagulation potential is determined by a method comprising:

(i) contacting an activator reagent with a sample of the body fluid, wherein the reagent reacts with the body fluid, said reagent comprising:
  (a) a predetermined amount of factor Xa or a hematologically equivalent mutant thereof; and
  (b) a predetermined amount of factor Va, a hematologically equivalent mutant thereof, or an enzyme which activates endogenous factor V;
(ii) if necessary, inducing coagulation by adding one or more coagulation accelerants; and
(iii) establishing a value indicative of the coagulation potential,
wherein the sample is diluted in plasma depleted only of a coagulant or anticoagulant component which is suspected to be present in the sample and the established value indicative of the coagulation potential is compared with that of the depleted plasma and/or normal plasma.

25. A method of determining a blood coagulation component or treatment additive in a sample containing a predetermined amount of human body fluid, comprising comparing the coagulation potential of the sample with that of a comparable normal human body fluid and/or that of a comparable human body fluid which either lacks the component or additive, or contains a known amount of the component or additive in excess, wherein coagulation potential is determined by a method comprising:
  (i) contacting an activator reagent with a sample of the body fluid, wherein the reagent reacts with the body fluid, said reagent comprising:
    (a) a predetermined amount of factor Xa or a hematologically equivalent mutant thereof; and
    (b) a predetermined amount of factor Va, a hematologically equivalent mutant thereof, or an enzyme which activates endogenous factor V;
  (ii) if necessary, inducing coagulation by adding one or more coagulation accelerants; and
  (iii) establishing a value indicative of the coagulation potential,
  wherein the sample is diluted in normal plasma, a plasma fraction or one or more coagulation factors to reduce the influence of matrix effects.

26. A method of determining a blood coagulation component or treatment additive in a sample containing a predetermined amount of human body fluid, comprising comparing the coagulation potential of the sample with that of a comparable normal human body fluid and/or that of a comparable human body fluid which either lacks the component or additive, or contains a known amount of the component or additive in excess, wherein coagulation potential is determined by a method comprising:
  (i) contacting an activator reagent with a sample of the body fluid, wherein the reagent reacts with the body fluid, said reagent comprising:
    (a) a predetermined amount of factor Xa or a hematologically equivalent mutant thereof; and
    (b) a predetermined amount of factor Va, a hematologically equivalent mutant thereof, or an enzyme which activates endogenous factor V;
  (ii) if necessary, inducing coagulation by adding one or more coagulation accelerants; and
  (iii) establishing a value indicative of the coagulation potential,
  wherein the sample is treated with a substance which inactivates heparin or heparin-like substances thereby enhancing specificity to non-heparin anticoagulants.

27. A method of monitoring the condition of a patient treated with a medication indicative of having a coagulant effect or anticoagulant effect, comprising determining the blood coagulation potential of a sample containing known quantity of body fluid from the patient by a method comprising:
  (i) contacting an activator reagent with a sample of the body fluid, wherein the reagent reacts with the body fluid, said reagent comprising:
    (a) a predetermined amount of factor Xa or a hematologically equivalent mutant thereof; and
    (b) a predetermined amount of factor Va, a hematologically equivalent mutant thereof, or an enzyme which activates endogenous factor V;
  (ii) if necessary, inducing coagulation by adding one or more coagulation accelerants; and
  (iii) establishing a value indicative of the coagulation potential,
  wherein the medication indicative of having an anticoagulant effect contains an anticoagulant selected from natural or synthetic inhibitors of factor Xa and/or thrombin.

28. A method of monitoring the condition of a patient treated with a medication indicative of having a coagulant effect or anticoagulant effect, comprising determining the blood coagulation potential of a sample containing known quantity of body fluid from the patient by a method comprising:
  (i) contacting an activator reagent with a sample of the body fluid, wherein the reagent reacts with the body fluid, said reagent comprising:
    (a) a predetermined amount of factor Xa or a hematologically equivalent mutant thereof; and
    (b) a predetermined amount of factor Va, a hematologically equivalent mutant thereof, or an enzyme which activates endogenous factor V;
  (ii) if necessary, inducing coagulation by adding one or more coagulation accelerants; and
  (iii) establishing a value indicative of the coagulation potential,
  wherein the medication indicative of having an anticoagulant effect contains an anticoagulant selected from unfractionated heparin (UFH), low molecular weight heparins (LMWH), heparinoids, dermatan sulphate, argatroban, modified hirudin and hirudin.

29. A method of monitoring the condition of a patient treated with a medication indicative of having a coagulant effect or anticoagulant effect, comprising determining the blood coagulation potential of a sample containing known quantity of body fluid from the patient by a method comprising:
  (i) contacting an activator reagent with a sample of the body fluid, wherein the reagent reacts with the body fluid, said reagent comprising:
    (a) a predetermined amount of factor Xa or a hematologically equivalent mutant thereof; and
    (b) a predetermined amount of factor Va, a hematologically equivalent mutant thereof, or an enzyme which activates endogenous factor V;
  (ii) if necessary, inducing coagulation by adding one or more coagulation accelerants; and
  (iii) establishing a value indicative of the coagulation potential,
  wherein the medication indicative of having a coagulant effect or anticoagulant effect contains an antibody against one or more blood coagulation components.

* * * * *